(12) United States Patent
Young

(10) Patent No.: US 8,084,195 B2
(45) Date of Patent: Dec. 27, 2011

(54) METHOD OF PERFUSING AN ORGAN WITH A SOLUTION COMPRISING A PEPTIDE WHICH INHIBITS PROTEIN KINASE C βII

(75) Inventor: Lindon H. Young, Philadelphia, PA (US)

(73) Assignee: Philadelphia College of Osteopathic Medicine, Philadelphia, PA (US)

( * ) Notice: Subject to any disclaimer, the term of this patent is extended or adjusted under 35 U.S.C. 154(b) by 748 days.

(21) Appl. No.: 11/905,219

(22) Filed: Sep. 28, 2007

(65) Prior Publication Data

US 2008/0311553 A1 Dec. 18, 2008

(51) Int. Cl.
*A01N 1/02* (2006.01)
(52) U.S. Cl. .......................................... 435/1.2
(58) Field of Classification Search .................. None
See application file for complete search history.

(56) References Cited

U.S. PATENT DOCUMENTS

| | | | |
|---|---|---|---|
| 6,054,261 A | 4/2000 | Masterson | |
| 6,447,539 B1 | 9/2002 | Nelson et al. | |
| 6,524,785 B1 | 2/2003 | Cozzone et al. | |
| 6,664,266 B2 | 12/2003 | He et al. | |
| 7,265,092 B2 * | 9/2007 | Li | 514/1.2 |
| 2002/0164795 A1 | 11/2002 | Gen | |

FOREIGN PATENT DOCUMENTS

WO WO-9817299 4/1998

OTHER PUBLICATIONS

Gschwendt et al., "Tyrosine phosphorylation and stimulation of protein kinase C delta from porcine spleen by src in vitro", FEBS Letters 347 : 85-89 (1994).*
Ito et al., "Vinculin phosphorylation by the SRC kinase: inhibition by chlorpormazine, imipramine and local anesthetics", BBRC 107(2) : 670-5 (1982), abstract only.*
Young et al., "Caveolin-1 peptide exerts cardioprotective effects in myocardial ischemia-reperfusion via nitric oxide mechanism", Am. J. Physiol. Heart Circ. Physiol. 280 :2489-2495 (2001).*
Johnson et al. "A Protein Kinase C Translocation Inhibitor as an Isozyme-selective Antagonist of Cardiac Function." The Journal of Biological Chemistry. Oct. 4, 1996, pp. 24962-24966, vol. 271, No. 40, The American Society for Biochemistry and Molecular Biology, Inc., U.S.A.
Inagaki et al. (2003). Additive protection of the ischemic hear ex vivo by combined treatment with delta-proteiin kinase C inhibitor and epsilon-protein kinase C activator. Circulation 108:869-875.
Chen et al. (2001). Opposing cardioprotective actions and parallel hypertrophic effect of deltaPKC and epsilonPKC. PNAS 98(20):11114-11119.
Young et al. (2001). Protein Kinase inhibition exerts cardioprotective effects in myocardial ischemia/reperfusion via inhibition of superoxide release. Methods Find Exp Clin Pharmacol 23(3):107-114.
Ron et al. (1995). C2 region-derived peptides inhibit translocation and function of beta protein kinase C in vivo. J. Biol. Chem. 270(41):24180-24187.
Dang et al. (2001). Protein kinase C sigma phosphorylates a subset of selective sites of the NADPH oxidase component p47phox and participates in formyl peptide-mediated neutrophil respiratory burst. J. Immunol. 166:1206-1213.
Peterman et al. (2004). Go 6983 exerts cardioprotective effects in myocardial ischemia/refperfusion. J. Cardiovasc. pharmacol. 43(5):645-656.
Oka, et al., "Caveolin Interaction with Protein Kinase C," Journal of Biological Chemistry, 1997, pp. 33416-33421, vol. 272, No. 52, The American Society for Biochemistry and Molecular Biology, Inc., Bethesda, MD, USA.
Barman, et al., "PKC Activates BKCa Channels in Rat Pulmonary Arterial Smooth Muscle Via cGMP-Dependent Protein Kinase," American Journal of Physiology—Lung Cellular and Molecular Physiology, 2004, pp. L1275-L1281, vol. 286, American Physiological Society, Bethesda, MD, USA.

* cited by examiner

*Primary Examiner* — Sandra Saucier
(74) *Attorney, Agent, or Firm* — Blank Rome LLP

(57) ABSTRACT

The present invention relates to a solution for preservation, perfusion, and/or reperfusion of an organ, especially the heart, for transplantation. The solution contains peptide inhibitor(s) of protein kinase C βII (PKC βII) and/or of protein kinase C ζ (PKC ζ) and/or peptide activator(s) of protein kinase C δ (PKCδ). Methods for using the inventive solution are also disclosed, including methods for preserving an organ for transplantation, for protecting an ischemic organ from damage, for attenuating organ dysfunction after ischemia, for maintaining nitric oxide release and/or inhibiting superoxide release in an ischemic organ, and for protecting an organ from damage when isolated from the circulatory system.

9 Claims, 26 Drawing Sheets

SEQUENCE LISTING

<160> NUMBER OF SEQ ID NOS: 3

<210> SEQ ID NO 1
<211> LENGTH: 9
<212> TYPE: PRT

-continued

```
<213> ORGANISM: Homo sapiens

<400> SEQUENCE: 1

Ser Leu Asn Pro Glu Trp Asn Glu Thr
1               5

<210> SEQ ID NO 2
<211> LENGTH: 13
<212> TYPE: PRT
<213> ORGANISM: Homo sapiens

<400> SEQUENCE: 2

Ser Ile Tyr Arg Arg Gly Ala Arg Arg Trp Arg Lys Leu
1               5                   10

<210> SEQ ID NO 3
<211> LENGTH: 8
<212> TYPE: PRT
<213> ORGANISM: Homo sapiens

<400> SEQUENCE: 3

Met Arg Ala Ala Glu Asp Pro Met
1               5
```

METHOD OF PERFUSING AN ORGAN WITH A SOLUTION COMPRISING A PEPTIDE WHICH INHIBITS PROTEIN KINASE C βII

The subject invention was made with government support under Grant No. 1R15 HL076235-01, awarded by the National Institute of Health. The government has certain rights in this invention.

FIELD OF THE INVENTION

The present invention relates to a solution for preservation, perfusion, and/or reperfusion of an organ, especially the heart, for transplantation. The solution contains peptide inhibitor(s) of protein kinase C beta II (PKC βII) and/or of protein kinase C zeta (PKC ζ) and/or peptide activator(s) of protein kinase C delta (PKC δ).

BACKGROUND OF THE INVENTION

Successful organ transplantation is often limited due to ischemic/reperfusion injury. Isolated human hearts deprived of oxygen for more than four hours progressively loose vigor and often do not survive in recipient hosts. Other organs such as the kidney, liver, pancreas and lung are also subject to tissue and cellular damage when removed from their hosts prior to transplantation. This damage is due to hypoxic conditions and a lack of circulation, which normally delivers physiological concentrations of oxygen and nutrients, and removes toxic compounds produced by an organ's cells. Organ transplants have a higher frequency of success when performed immediately after excision from their hosts.

Recent advances have increased the rate of successful organ transplants and organ surgery, such as coronary bypass surgery. The first includes organ preservation and organ perfusion solutions. The second is improved methods and devices for the delivery of organ perfusion solutions to an organ.

Short-term myocardiac preservation is currently provided by cold storage after cardioplegic arrest. A variety of processes exist however differing by the composition of the solution used, the preservation temperature and the administration protocol. Different solutions for arresting and preserving the heart have been developed to protect the myocardium in cardiac surgery. Examples of these solutions include Krebs-Henseleit solution, UW solution, St. Thomas II solution, Collins solution and Stanford solution. (See, for example, U.S. Pat. Nos. 4,798,824 and 4,938,961; Southard and Belzer, *Ann. Rev. Med.* 46:235-247 (1995); and Donnelly and Djuric, *Am. J. Hosp. Pharm.* 48:2444-2460 (1991)). Nevertheless, organ rejections still remains due to deterioration in the condition of the transplanted organ between the time of removal and the restoration of blood flow in the recipient.

Restoration of blood flow is the primary objective for treatment of organ tissue experiencing prolonged ischemia, e.g., during transplant. However, reperfusion of blood flow induces endothelium and myocyte injury, resulting in organ dysfunction (Buerke et al., *Am J Physiol* 266: H128-136, 1994; Lucchesi and Mullane, *Ann Rev Pharmacol Toxicol* 26: 2011-2024, 1986; and Lucchesi et al., *J Mol Cell Cardiol* 21: 1241-1251, 1989). The sequential events associated with reperfusion injury are initiated by endothelial dysfunction which is characterized by a reduction of the basal endothelial cell release of nitric oxide (NO) within the first 2.5-5 min post-reperfusion (Tsao and Lefer, *Am J Physiol* 259: H1660-1666, 1990). The decrease in endothelial derived NO is associated with adhesion molecule up-regulation on endothelial and polymorphonuclear (PMN) leukocyte cell membranes (Ma et al., *Circ Res* 72: 403-412, 1993; and Weyrich et al., *J Leuko Biol* 57: 45-55, 1995). This event promotes PMN/endothelial interaction, which occurs by 10 to 20 min post-reperfusion, and subsequent PMN infiltration into the myocardium is observed by 30 min post reperfusion (Lefer and Hayward, In *The Role of Nitric Oxide in Ischemia-Reperfusion: Contemporary Cardiology*, Loscalzo et al. (Eds.), Humana Press, Totowa, N.J., pp. 357-380, 2000; Lefer and Lefer, *Cardiovasc Res* 32: 743-751, 1996; Tsao et al., *Circulation* 82: 1402-1412, 1990; and Weyrich et al., *J Leuko Biol* 57: 45-55, 1995).

Chemotactic substances released from reperfused tissue and plasma factors activate PMNs that augment PMN release of cytotoxic substances (i.e. superoxide anion) and contribute to organ dysfunction following ischemia/reperfusion (Lucchesi et al. *J Mol Cell Cardiol* 21: 1241-1251, 1989; Ma et al., *Circ Res* 69: 95-106, 1991; Tsao et al., *Circulation* 82: 1402-1412, 1990; and Tsao et al., *Am Heart J* 123: 1464-1471, 1992). Superoxide combines with NO to produce peroxynitrite anion thus reducing the bioavailability of NO and promotes endothelial dysfunction and PMN infiltration after myocardial ischemia/reperfusion (Clancey et al., *J Clin Invest* 90: 1116-1121, 1992; Hansen, *Circulation* 91: 1872-85, 1995; Lucchesi et al., *J Mol Cell Cardiol* 21: 1241-1251, 1989; Rubanyi and Vanhoutte, *Am J Physiol* 250: H815-821, 1986; Tsao et al., *Am Heart J* 123: 1464-1471, 1992; and Weiss, *New Eng J Med* 320: 365-375, 1989).

Therefore, there remains a need for a solution of improved quality that can extend the preservation time of an organ for transplantation and protect the organ from reperfusion injury after ischemia, so that the organ can resume proper function after restoration of blood flow.

SUMMARY OF THE INVENTION

The present invention provides a solution for preservation, perfusion, and/or reperfusion of an organ, especially the heart, containing peptide inhibitor(s) of protein kinase C βII (PKC βII) and/or of protein kinase C ζ (PKC ζ) and/or peptide activator(s) of protein kinase C δ (PKC δ). The solution protects organ tissues and cells from damage while the organ is isolated from the circulatory system or is experiencing decreased blood flow (ischemia). The present inventor has discovered that the peptide inhibitors of PKC βII and/or PKC ζ, and/or peptide activator(s) of PKC δ enhance NO release or inhibit endothelial/PMN superoxide release, which can exert protective effect in organs undergoing ischemia/reperfusion.

In an embodiment, the solution contains about 5-10 μM of the peptide inhibitor of PKC βII and/or about 2.5-5 μM of the peptide inhibitor of PKC ζ and/or a 5-10 μM of the peptide activator of PKC δ dissolved in a saline solution.

The solution of the present invention can be used as a perfusion solution or a preservation solution. As a perfusion solution, it is pumped into the vasculature of the organ to protect the organ tissues and cells. As a preservation solution, it serves as a bathing solution into which the organ is submerged. Preferably, the organ is perfused with and submerged in the present solution. Further, the present solution also serves as a reperfusion solution upon restoration of blood flow to the organ after ischemia.

The present invention also include methods of using the solution of the present invention. These include methods for preserving an organ for transplantation, for protecting an ischemic organ from damage, for attenuating organ dysfunction after ischemia, for maintaining nitric oxide release in an ischemic organ, and for protecting an organ from damage when isolated from the circulatory system.

DETAILED DESCRIPTION OF THE PREFERRED EMBODIMENT

Figure 1:
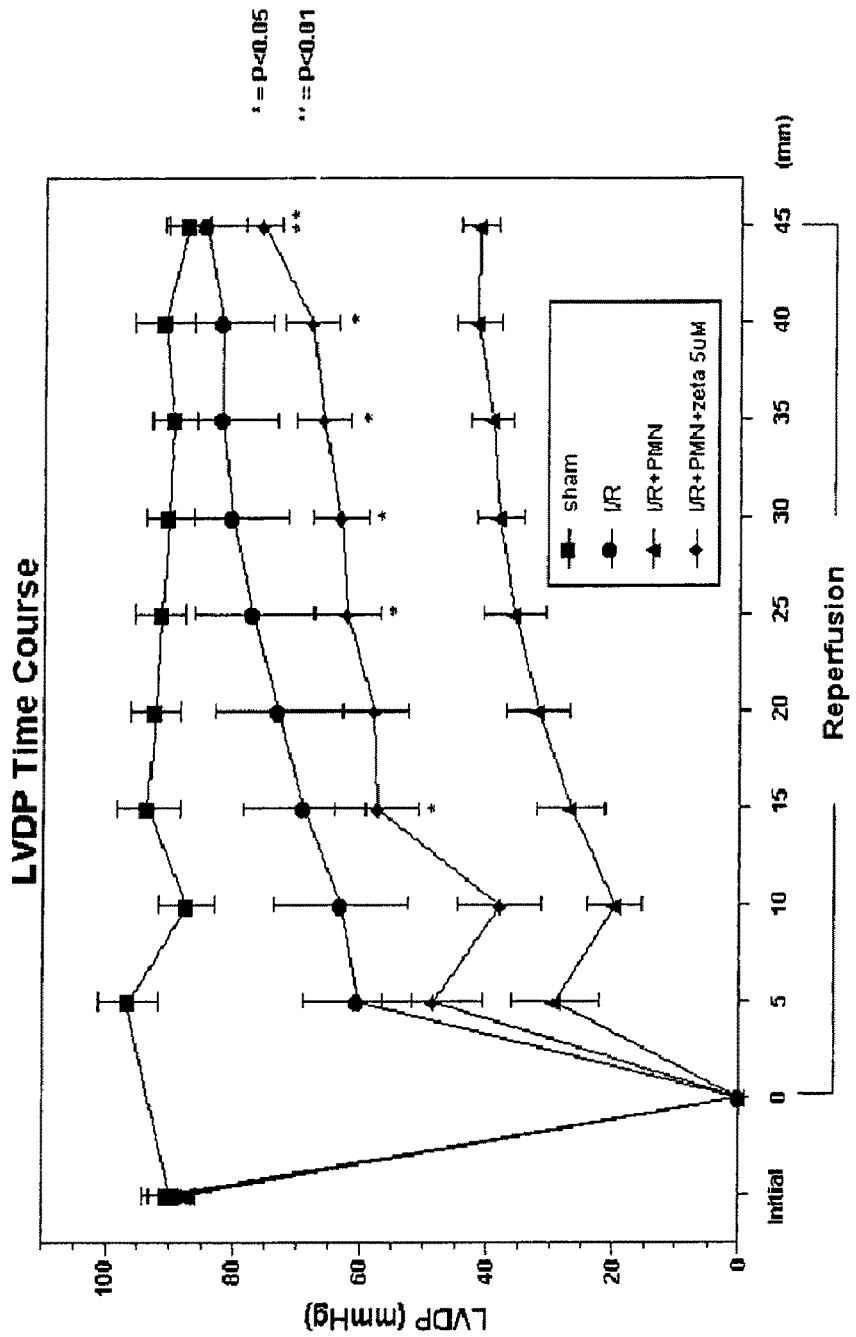
FIG. 1. Time course of LVDP (left ventricular developed pressure=left ventricular end systolic pressure—left ventricular end diastolic pressure) in sham, I/R, I/R+PMNs and I/R+PMN+PKCζ peptide inhibitor (5 μM) perfused rat hearts. LVDP data at initial (baseline) and reperfusion from 0 to 45 min following 20 min ischemia. The sham group (n=6) maintained the same LVDP throughout the 80 min. protocol. The I/R (n=6) group recovered to initial baseline values. I/R+PMN group (n=6) exhibited a significant and sustained reduction in LVDP compared to and I/R+PMN+PKCζ peptide inhibitor (n=6) group. All values are expressed as mean±SEM. *$p<0.05$ and **$p<0.01$, I/R+PMN+PKCζ peptide inhibitor group from I/R+PMNs.

The present invention provides a solution for the preservation, perfusion, and/or reperfusion of an organ, especially the heart. The solution contains peptide inhibitor(s) of protein kinase C βII (PKC βII) and/or of protein kinase C ζ (PKC ζ) and/or peptide activator(s) of PKC δ. Preferably, the peptide inhibitor of PKC βII or the peptide activator of PKC δ is present in the solution in an amount of about 5-10 μM; and the peptide inhibitor of PKC ζ is present in an amount of about 2.5-5 μM.

In a preferred embodiment, the peptide inhibitor of PKC βII has an amino acid sequence of SEQ ID NO: 1; the peptide inhibitor of PKC ζ has an amino acid sequence of SEQ ID NO: 2; and the peptide activator has an amino acid sequence of SEQ ID NO: 3. Also, in other embodiments, it is preferred that the peptide inhibitor/activator is myristoylated to facilitate absorption into the cells of the organ.

In a preferred embodiment, the peptide inhibitor(s) or peptide activator (s) are dissolved in a saline solution, preferably normal saline (0.9% NaCl). The peptide inhibitor(s) can also be dissolved in known preservation solution, such as Krebs-Henseleit solution, UW solution, St. Thomas II solution, Collins solution, Stanford solution, and the like. The solution may also contain one or more of sodium ($Na^+$), potassium ($K^+$), calcium ($Ca^{2+}$), magnesium ($Mg^{2+}$), glutamate, arginine, adenosine, manitol, allopurinol, glutathione, raffinose, and lactobionic acid in concentrations of about 4-7 mM, about 0.2-0.3 mM, about 108-132 mM, about 13-16 mM, about 18-22 mM, about 2-4 mM, about 0.5-1 mM, about 27-33 mM, about 0.9-1.1 mM, about 2.7-3.3 mM, about 25-35 mM, and about 80-120 mM, respectively. $Na^+$ can be in the form of NaOH; $K^+$ can be in the form of KCl and/or $KH_2PO_4$, most preferably at ratio of about 2-3.5 mM KCl and about 2-3.5 mM $KH_2PO_4$; $Ca^{2+}$ can be in the form of $CaCl_2$; and $Mg^{2+}$ can be in the form of $MgCl_2$. The solution is preferably maintained at physiological pH of about 7.2-7.4.

The solution of the present invention can be used during all phases of an organ, especially the heart, transplant, including, but are not limited to, 1) isolating of the organ from the donor (cardioplegic solution); 2) preserving the organ (hypothermic storage/transport); and 3) re-implanting the organ in the recipient (reperfusion solution).

During perfusion or reperfusion, especially for the heart, it is preferred that the organ be perfused at a rate of about 1 mL/min for about 5 min. The perfusion rate can be varied, but it should not exceed about 25 mL/min. Overall, the perfusion rate should not be so high as to impose undue pressure on the vasculature of the organ.

The solution of the present invention can be prepared by 1) dissolving and diluting the peptide inhibitor(s) and the different constituents in distilled water; 2) adjusting the pH to about 7.2-7.4, e.g. with NaOH; and 3) sterilizing the solution, e.g., by filtering with a 0.2 μm filter. The sterilized solution is then kept isolated from contaminants in the environment.

Without further description, it is believed that one of ordinary skill in the art can, using the preceding description and the following illustrative examples, make and utilize the compounds of the present invention and practice the claimed methods. The following example is given to illustrate the present invention. It should be understood that the invention is not to be limited to the specific conditions or details described in this example.

Example 1

Effects of Peptide Inhibitor of PKC ζ

Male Sprague Dawley rats (275-325 g, Ace Animals, Boyertown, Pa.) were anesthetized with 60 mg/kg pentobarbital sodium intraperitoneally (i.p.). Sodium heparin (1,000 U) was also administered i.p. The hearts were rapidly excised, the ascending aortas were cannulated, and retrograde perfusion of the heart was initiated with a modified Krebs buffer maintained at 37° C. at a constant pressure of 80 mmHg. The Krebs buffer had the following composition (in mmol/l): 17 dextrose, 120 NaCl, 25 $NaHCO_3$, 2.5 $CaCl_2$, 0.5 EDTA, 5.9 KCl, and 1.2 $MgCl_2$. The perfusate was aerated with 95% $O_2$ and 5% $CO_2$ and equilibrated at a pH of 7.3-7.4. The two side arms in the perfusion line proximal to the heart inflow cannula allowed PMNs, plasma without PKC ζ peptide inhibitor (control hearts) or plasma containing different concentrations of PKC ζ peptide inhibitor (1, 2.5 or 5 μM) to be directly infused into the coronary inflow line. Coronary flow was monitored by a flow meter (T106, Transonic System, Inc., Ithaca, N.Y.).

LVDP and $+dP/dt_{max}$ were monitored using a pressure transducer (SPR-524, Millar Instruments, Inc., Houston, Tex.), which was positioned in the left ventricular cavity. Hearts were immersed in a water-jacketed reservoir containing 160 mL of Krebs buffer maintained at 37° C. Coronary flow, LVDP and $+dP/dt_{max}$ were recorded using a Powerlab Station acquisition system (ADInstruments, Grand Junction, Colo.) in conjunction with a computer.

LVDP, $+dP/dt_{max}$, and coronary flow were measured every 5 min for 15 min to equilibrate the hearts and obtain a baseline measurement. LVDP was defined as left ventricular end-systolic pressure minus left ventricular end-diastolic pressure. After 15 min, the flow of the Krebs buffer was reduced to zero for 20 min to induce global ischemia. At reperfusion, hearts were infused for 5 min with $200 \times 10^6$ PMN resuspended in 5 mL of Krebs buffer plus 5 mL of plasma at a rate of 1 mL/min. In some experiments, PKCζ peptide inhibitor (Genemed Synthesis, Inc., San Francisco, Calif.) was added to plasma at a final concentration of 1, 2.5 or 5 μM. Sham I/R hearts were not subjected to ischemia and were not perfused with PMNs.

The following groups of isolated perfused rat hearts were used:

Group 1: Sham Ischemia/Reperfusion (I/R) hearts was not subjected to ischemia and not perfused with PMNs, but was perfused with 5 mL of plasma (1 mL/min) at 35 minutes into perfusion (the same time point that I/R hearts would be given 5 mL of plasma, 15 minutes of baseline recordings plus 20 minutes ischemia). These hearts represented a control group to determine if the isolated rat heart can maintain LVDP and $+dP/dt_{max}$ throughout the 80-minute protocol (n=6).

Group 2: Sham I/R+PKC ζ peptide inhibitor (5 μM) hearts were not subjected to ischemia and not perfused with PMNs. These hearts were administered the PKC ζ peptide inhibitor (5 μM, dissolved in plasma from a 5 mM stock in $H_2O$) 35 minutes into perfusion. This group was employed to determine if the PKC ζ peptide inhibitor causes a cardiotonic or cardiodepressant effect (n=6).

Group 3: I/R hearts were subjected to 20 min of ischemia and perfused with 5 mL of plasma (1 mL/min) during the first 5 min of reperfusion, but were not perfused with PMNs. These hearts represented a control group to determine if 20 min of ischemia followed by reperfusion stuns the heart, but LVDP and $+dP/dt_{max}$ will recover to baseline values (initial) by the end of the 45-minute reperfusion period (n=6).

Group 4: I/R+PKC ζ peptide inhibitor (5 μM, dissolved in plasma) hearts were subjected to 20 min. of ischemia and not perfused with PMNs. These hearts were perfused with 5 mL of plasma+PKC ζ inhibitor during the first 5 min of reperfusion. This group was employed to determine if the PKC ζ peptide inhibitor caused a cardiodepressant effect in the setting of I/R without PMNs (n=6).

Group 5: I/R+PMNs hearts were subjected to 20 min of ischemia and perfused with 5 mL of plasma (1 mL/min) and PMNs (resuspended in 5 mL Krebs buffer) during the first 5 min of reperfusion. These hearts represented a control group to determine if 20 min of ischemia followed by 45 min reperfusion in the presence of PMNs ($200 \times 10^6$) resulted in a sustained cardiac contractile dysfunction throughout the 45 min reperfusion period compared to initial baseline values (n=6).

Group 6: I/R+PMNs+PKC ζ peptide inhibitor (1 μM) hearts were subjected to 20 min of ischemia and perfused with 1 μM PKC ζ peptide inhibitor (dissolved in plasma) and PMNs ($200 \times 10^6$) during the first 5 minutes of reperfusion. These hearts represented a group to determine the effect of PKC ζ inhibition in attenuating PMN-induced cardiac contractile dysfunction (n=6).

Group 7: I/R+PMNs+PKC ζ peptide inhibitor (2.5 μM) hearts were subjected to 20 min of ischemia and perfused with 2.5 μM PKC ζ peptide inhibitor (dissolved in plasma) and PMNs (200×10⁶) during the first 5 minutes of reperfusion. These hearts represented a group to determine the effect of PKC ζ inhibition in attenuating PMN-induced cardiac contractile dysfunction (n=6).

Group 8: I/R+PMNs+PKC ζ peptide inhibitor (5 μM) hearts were subjected to 20 min of ischemia and are perfused with 5 μM PKC ζ peptide inhibitor (dissolved in plasma) and PMNs (200×10⁶) during the first 5 minutes of reperfusion. These hearts represented a group to determine the effect of PKC ζ inhibition at a higher concentration of the PKC t peptide inhibitor in attenuating PMN-induced cardiac contractile dysfunction (n=6).

Group 9: I/R+PMNs+PKC ζ peptide inhibitor (5 μM)+$N^G$-nitro-L-arginine methyl ester (L-NAME, 50 μM) hearts were subjected to 20 min of ischemia and perfused with 5 μM PKC ζ peptide inhibitor (dissolved in 5 mL plasma) and 50 μM L-NAME (dissolved in Krebs buffer from 50 mM stock in $H_2O$) and PMNs (200×10⁶) during the first 5 minutes of reperfusion. The L-NAME (50 μM) was continually infused into the heart throughout the 45 min reperfusion period. These hearts represent a group to determine if the cardioprotective effect of PKC ζ peptide inhibition could be blocked with a nitric oxide synthase inhibitor (L-NAME) (n=5).

Data were recorded every 5 min for 45 min post-reperfusion. After each experiment, the left ventricle was isolated, fixed in 4% paraformaldehyde and stored at 4° C. for later histological analysis.

FIG. 1 showed the time course of cardiac contractile function (i.e., LVDP). The data from the sham I/R, I/R, I/R+PMN+PKC ζ peptide inhibitor (5 μM) and I/R+PMN groups illustrated the relative changes in LVDP during the 80 min perfusion period. As shown, the sham I/R remained near or greater than 100% of initial baseline values of LVDP for the entire perfusion period. The I/R hearts experienced a depression in LVDP at the beginning of reperfusion, but recovered to 95±7% of initial baseline values by the end of reperfusion. In contrast, the I/R+PMN hearts suffered severe cardiac contractile dysfunction, recovering to only 47±7% of initial baseline values by 45 min post-reperfusion. Conversely, the I/R+PMN+PKC ζ peptide inhibitor (5 μM) hearts recovered to 84±4% at 45 min post-reperfusion.

To determine whether PKC ζ peptide inhibitor produced direct inotropic effects on cardiac contractile function, non-ischemic sham I/R hearts were perfused with PKC ζ peptide inhibitor (5 μM). Treatment of Sham I/R hearts with PKC ζ peptide inhibitor did not result in any significant change in LVDP (FIG. 2) or $+dP/dt_{max}$ (FIG. 3) during the 80 min perfusion period, demonstrating the PKC ζ peptide inhibitor at 5 μM exerts no direct effect on cardiac contractile function. A 15 μM PKC ζ peptide inhibitor concentration was initially tested, since this concentration corresponded with an 82% inhibition of PMN superoxide release. However, 15 μM produced a cardiodepressant effect (50% reduction in LVDP Sham I/R hearts) and could not be used in these experiments (data not shown).

Figure 2:
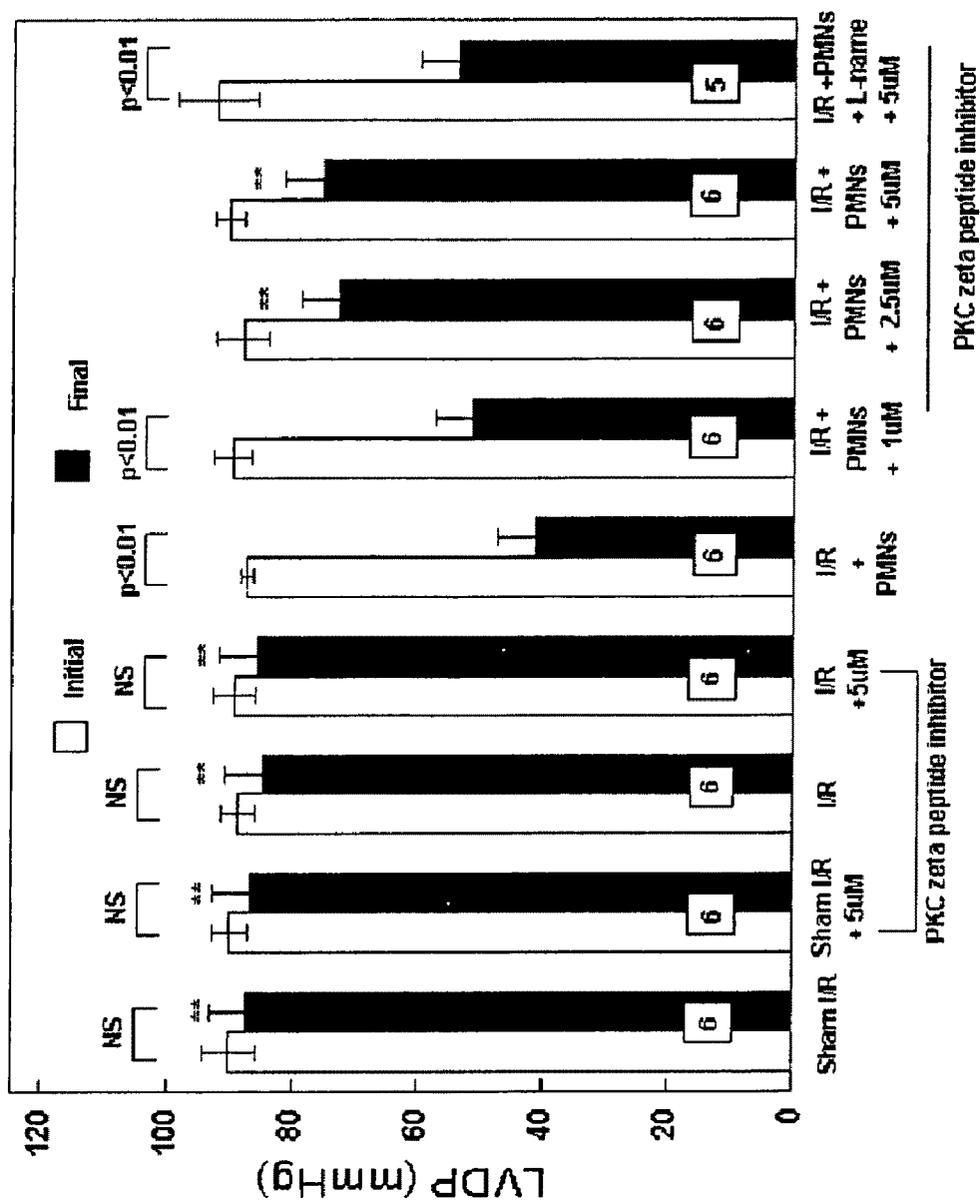
FIG. 2. Initial and final LVDP expressed in mmHg from isolated perfused rat hearts before ischemia (I) (initial) and after 45 min post reperfusion (R) (final). Hearts were perfused in the presence or absence or PMNs. PMNs induced a significant contractile dysfunction, which was attenuated by the PKCζ peptide inhibitor, but was significantly blocked by $N^G$-nitro-L-arginine methyl ester (L-NAME). All values are expressed as mean±SEM. Numbers of hearts examined are at the bottom of the bars. **$p<0.01$, from final I/R+PMNs; NS=not significant.
Figure 3:
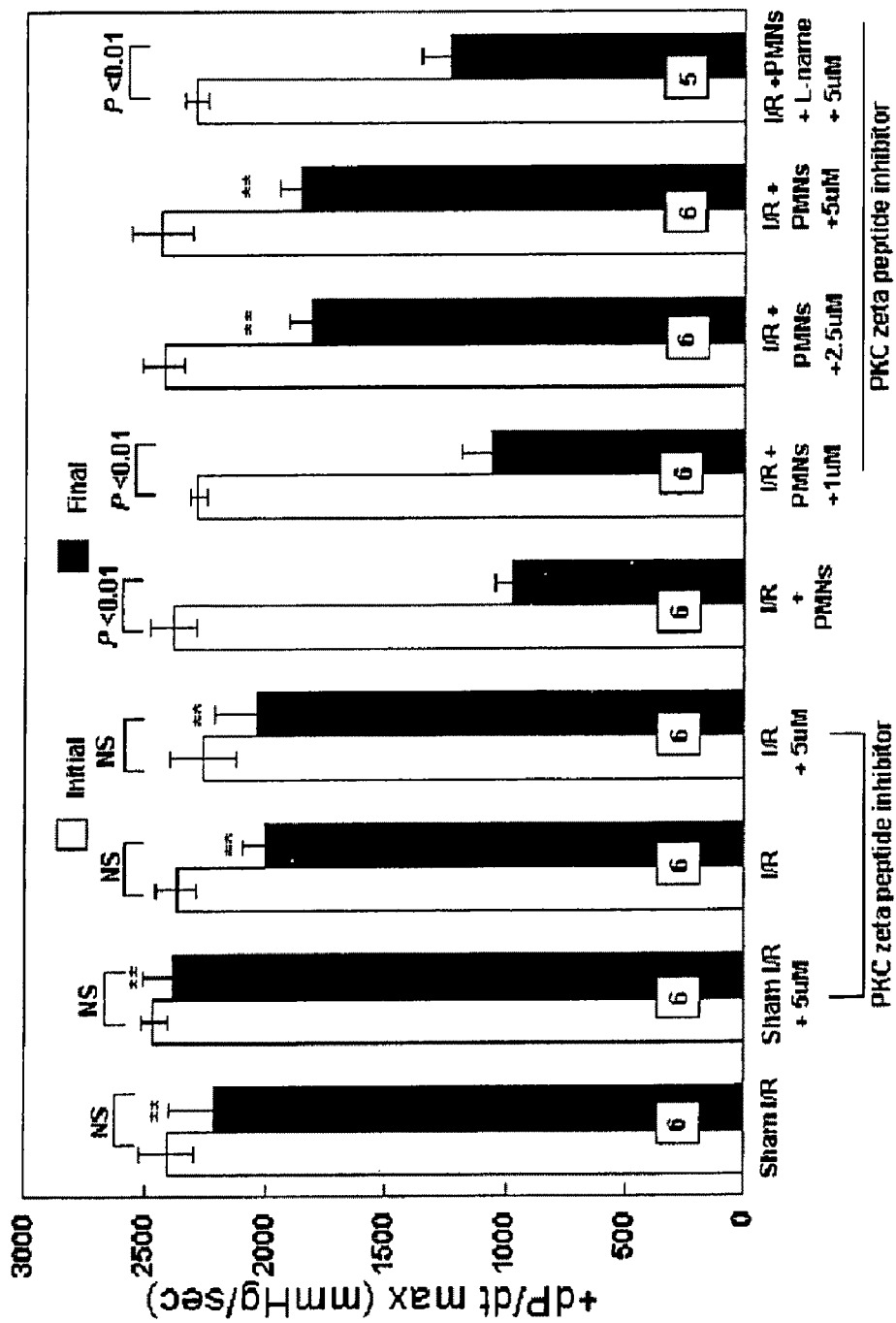
FIG. 3. Initial and final maximal rate of LVDP (+dP/dt max) expressed in mmHg/s in isolated perfused rat hearts before ischemia (I) and after reperfusion (R). Hearts were perfused in the presence or absence of PMNs. PMNs induced a significant contractile dysfunction, which was attenuated by a PKCζ peptide inhibitor, but was blocked by L-NAME. All values are expressed as means±SEM. Numbers of hearts examined are at the bottom of the bars. **$P<0.01$, from final I/R+PMNs; NS=not significant.

FIGS. 2 and 3 showed the initial and final values for LVDP and $+dP/dt_{max}$ from isolated perfused rat hearts. The initial baselines were similar for all groups. However, the final LVDP and $+dP/dt_{max}$ (45 min post-reperfusion) was significantly decreased (p<0.01) by 47±7% and 41±7% respectively for the I/R hearts reperfused with PMNs compared to its initial baseline. The PKC ζ peptide inhibitor (2.5 μM and 5 μM concentrations) significantly attenuated the decrease in LVDP and $+dP/dt_{max}$ associated with post-ischemic reperfusion with PMNs. In the group receiving 5 μM of drug, the hearts recovered to 84±4% and 76±5% for final LVDP and $+dP/dt_{max}$ compared to its initial baseline. The lowest effective dose was observed at 2.5 μM; and these hearts recovered to 83±4% for LVDP and 75±5% for $+dP/dt_{max}$ compared to initial baseline values. The cardioprotective effects of the PKC (peptide inhibitor (5 μM) were blocked in the presence of L-NAME (50 μM). These hearts only recovered to 58±7% and 54±9% for LVDP and $+dP/dt_{max}$, respectively, at 45 min post-reperfusion compared to its initial baseline. These hearts were similar to the IR+PMN group (47±7% and 41±7% LVDP, $+dP/dt_{max}$). At 1 μM, PKC ζ peptide inhibitor treated hearts exposed to I/R+PMNs only recovered to 57±10% and 46±6% for LVDP and $+dP/dt_{max}$, respectively, at 45 min post-reperfusion compared to its initial baseline. These hearts were not significantly different from control I/R+PMN hearts at 45 min post-reperfusion at this lower dose.

Figure 4A:
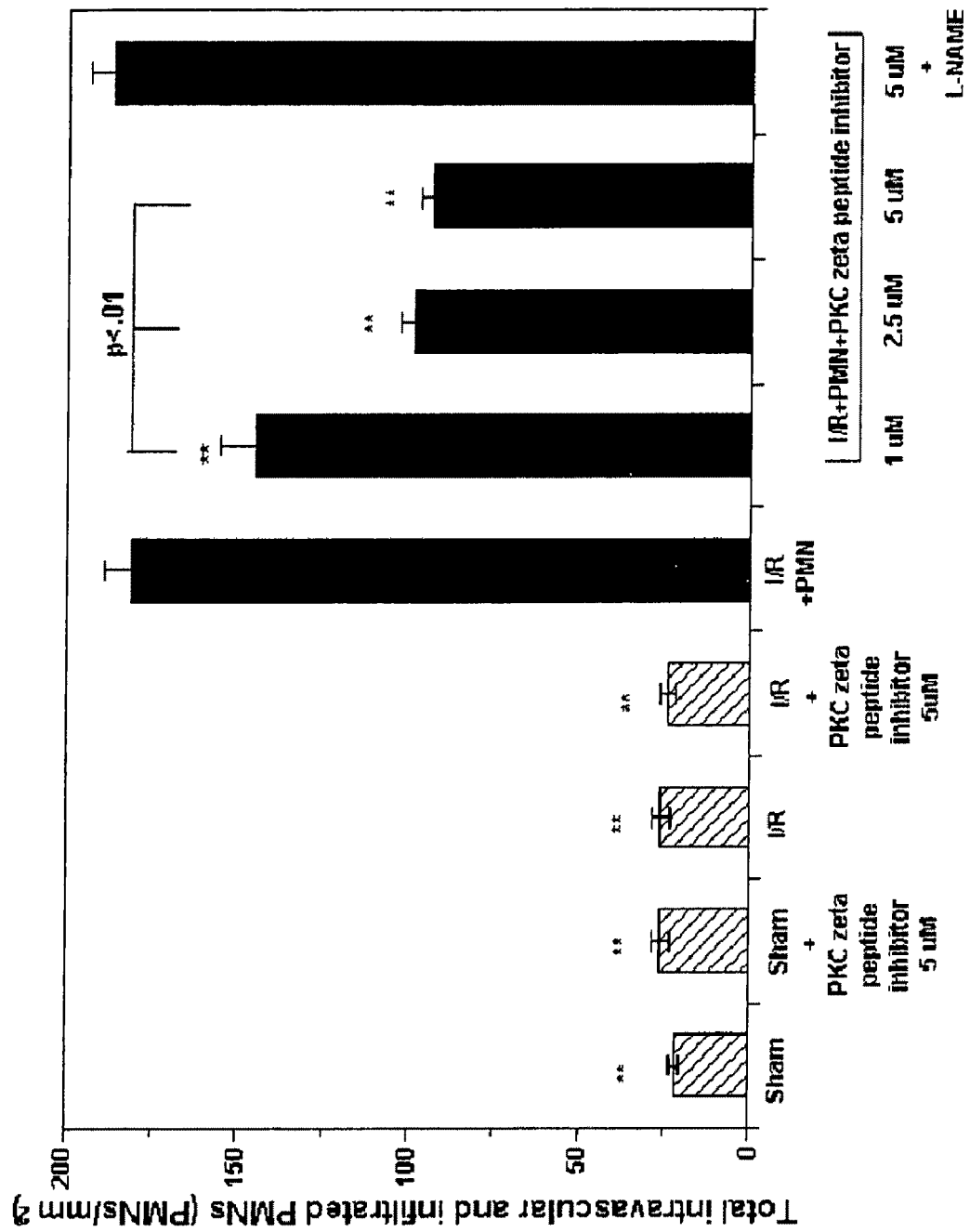
FIG. 4a. Histological assessment of total intravascular and infiltrated PMNs in isolated perfused rat heart samples taken from 3 rats per group and 10 areas per heart. The numbers of total intravascular and infiltrated PMNs in post-reperfusion cardiac tissue and adhering to coronary vasculature was significantly attenuated by the PKCζ peptide inhibitor. Hatched boxes represent non-PMN perfused hearts and black boxes represent PMN-perfused hearts. **$P<0.01$, from I/R+PMNs.

The cardiac injury associated with I/R in this model was closely correlated with the substantial number of PMNs infiltrating the myocardium within the 45 min reperfusion period. During reperfusion, a significant number of PMNs transmigrated into the myocardium, increasing from less than 25 PMN/mm² in Sham I/R hearts to more than 180 PMN/mm² in I/R+PMN hearts at the end of the reperfusion period (FIG. 4a). In contrast, I/R+PMN+PKC ζ peptide inhibitor treated hearts experienced a 20±6%, 46±4% and 48±3% significant reduction in PMN infiltration into the post-reperfused cardiac tissue at 1, 2.5 and 5 μM (p<0.01), respectively; and this effect was blocked in the presence of L-NAME. Furthermore, the 2.5 and 5 μM treated hearts had significantly fewer infiltrated PMNs compared to 1 μM treated hearts (p<0.01) (FIG. 4a).

Figure 4B:
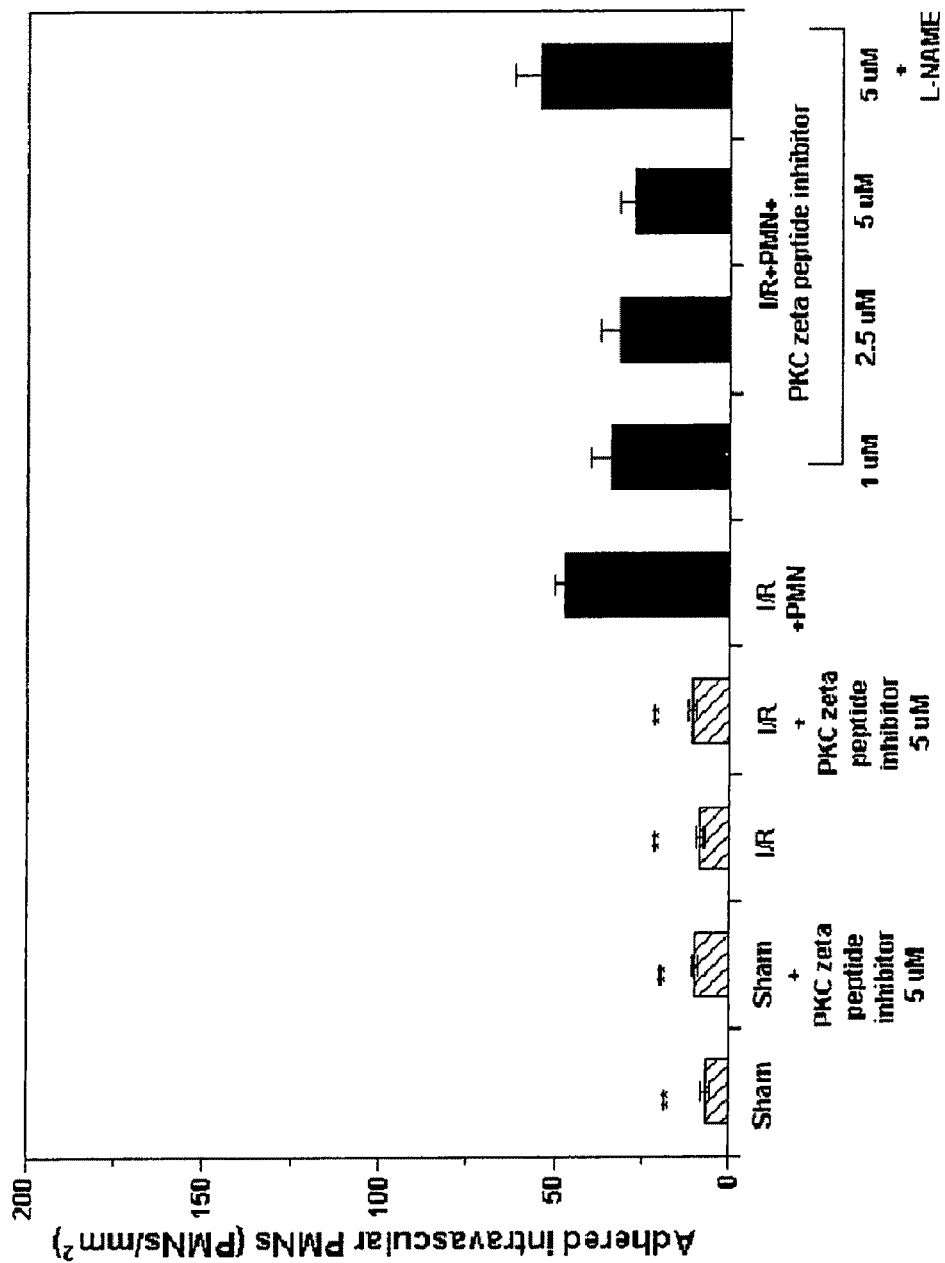
FIG. 4b. Histological assessment of intravascular PMNs that adhered to the coronary vasculature in isolated perfused rat heart samples taken from 3 rats per group and 10 areas per heart. The numbers of PMNs adhering to the coronary vasculature was not significantly different from I/R+PMNs. Hatched boxes represent non-PMN perfused hearts and black boxes represent PMN-perfused hearts. All values are mean numbers of PMNs/mm² of heart area±SEM.
Figure 5:
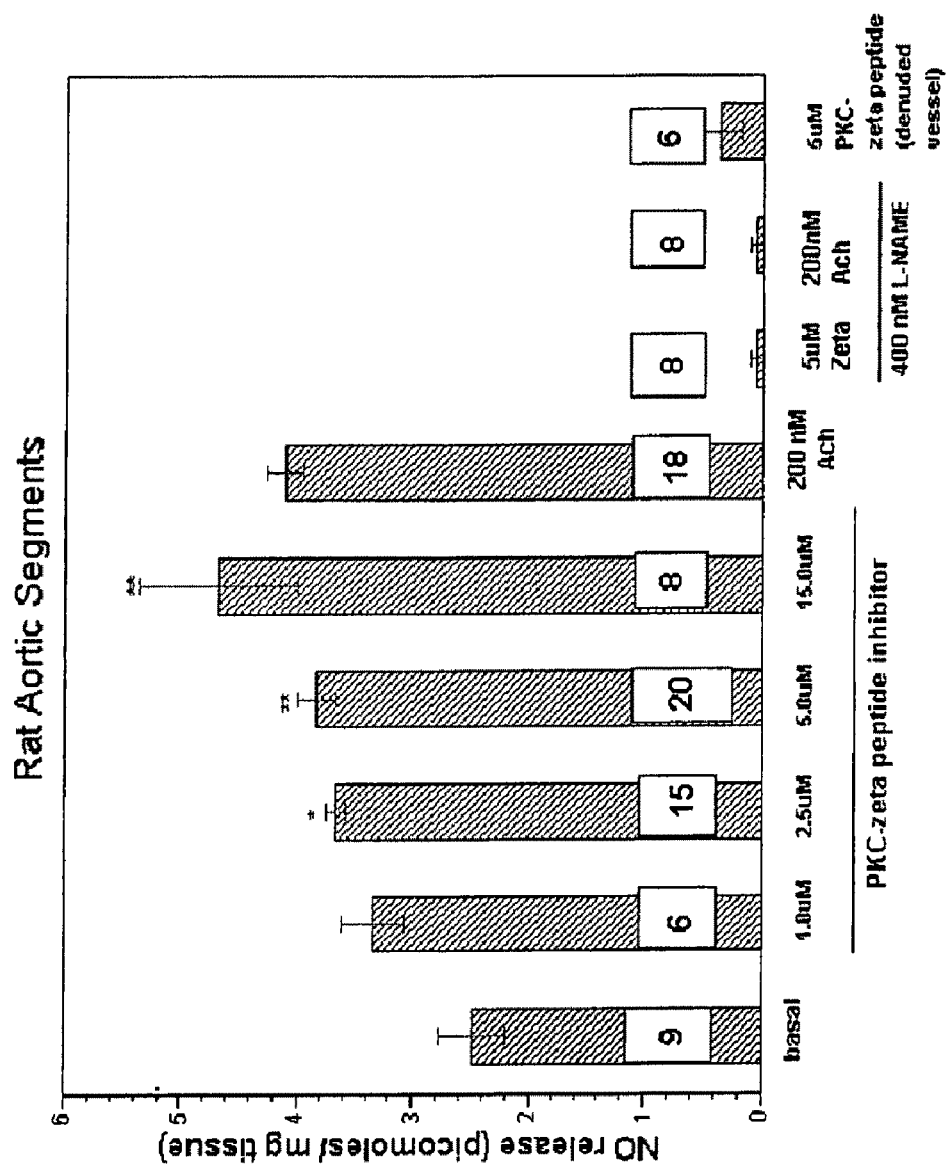
FIG. 5. Measurement of NO release from rat aortic segments. Endothelial NO release was significantly increased from basal NO release in PKCζ peptide inhibitor treated segments (2.5-15 μM), as well as acetylcholine (Ach, 200 nM). NO release was significantly reduced in both groups given 400 μM L-NAME, and in endothelium removed (denuded) segments. All values are expressed as means±SEM. Numbers at bottom of bars are numbers of separate experiments per group. *$p<0.05$, **$p<0.01$, from basal values.

PMN adherence to coronary vascular endothelium was also evaluated within the assessment of total intravascular and infiltrated PMNs. As seen in FIG. 4b, the number of adherent PMNs to the coronary endothelium was not significantly reduced in I/R+PMN+PKC ζ peptide inhibitor hearts (5 μM) (43±10%, p<0.06) (FIG. 4b). NO release from rat aortic endothelium was measured to determine if PKC ζ peptide inhibitor provides cardioprotection by a mechanism involving increased endothelial NO release. In FIG. 5, PKC ζ peptide inhibitor-treated endothelium generated significantly more NO by 47±2% (2.5 μM, p<0.05), 54±5% (5 μM, p<0.01), and 91±15% (15 μM, p<0.01) compared to basal NO release. At 1 μM, NO release was not significantly different from basal NO release. Acetylcholine (200 nM) was used as a positive control in the NO assay, and significantly increased NO release by 67±4% (p<0.01) compared to basal NO release. The eNOS inhibitor, L-NAME, was used as another control in order to decrease basal release of NO to zero. Both the acetylcholine and the PKC ζ peptide inhibitor-induced production of NO were completely inhibited by treating the endothelium with L-NAME (400 μM). To attribute the source of the NO to the endothelium, experiments with endothelium removed (denuded) rat aortic segments were incubated with PKC ζ peptide inhibitor (5 μM) and were not different from L-NAME-treated segments.

Figure 6:
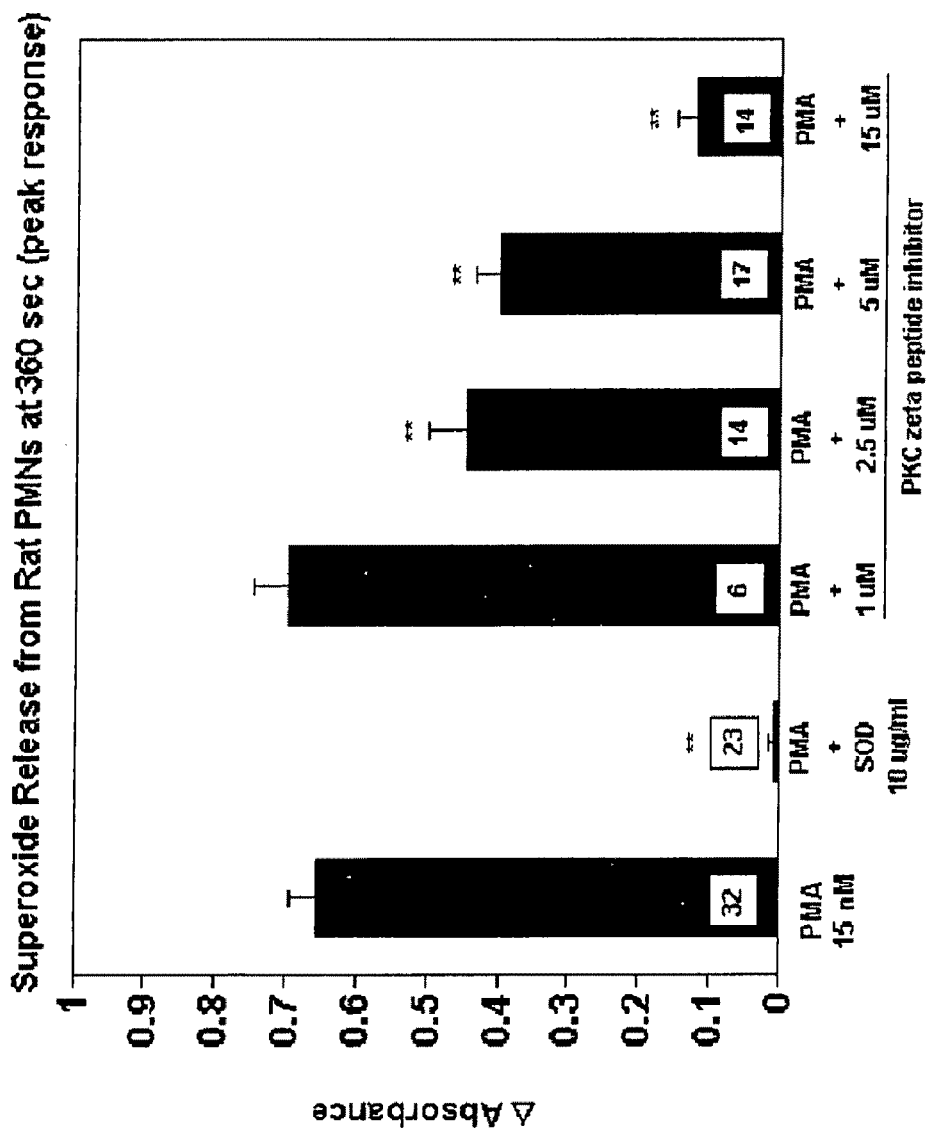
FIG. 6. Superoxide release from rat PMNs. Superoxide release was measured from $5\times10^6$ PMNs after phorbol-12-myristate-13-acetate (PMA) (15 nM) stimulation. Superoxide dismutase (SOD) (10 μg/ml) was employed as a positive control. The change in absorbance (Δ) was measured 360 sec after PMA addition (peak response). Superoxide release was significantly inhibited by the PKCζ peptide inhibitor (**$p<0.01$, 2.5, 5 and 15 μM). All values are means±SEM. Numbers at bottom of bars show the numbers of separate experiments per group.

Another mechanism of the cardioprotective effects of PKC ζ peptide inhibitor may be related to inhibition of superoxide release. PKC ζ peptide inhibitor significantly inhibited superoxide release by 33-82% (2.5-15 μM, p<0.01), except at 1 μM where there was no difference from suspensions of PMA-stimulated rat PMNs (FIG. 6). SOD (10 μg/mL) was used as a positive control in the superoxide assays, and degraded superoxide release produced by the PMA-stimulated rat PMNs by 99% (p<0.01; FIG. 6).

Example 2

Effects of Peptide Inhibitor of PKC βII

Experiments with PKCβ II peptide inhibitors were performed substantially as described in Example 1 for PKCζ peptide inhibitors.

The following groups of isolated perfused rat hearts were used:

Group 1: Sham I/R hearts were not subjected to ischemia and were not perfused with PMNs, but were perfused with 5 mL of plasma (1 mL/min) at 35 minutes into perfusion (the same time point that I/R hearts would be given 5 mL of plasma, 15 minutes of baseline recordings plus 20 minutes ischemia). These hearts represented a control group to determine if the isolated rat heart can maintain LVDP and +dP/$dt_{max}$ throughout the 80-minute protocol (n=6).

Group 2: Sham I/R+PKC βII peptide inhibitor (10 μM) hearts were not subjected to ischemia and not perfused with PMNs. These hearts were administered the PKC βII peptide inhibitor (10 μM, dissolved in plasma from a 5 mM stock in $H_2O$) 35 minutes into perfusion. This group was employed to determine if the PKC βII peptide inhibitor causes a cardiotonic or cardiodepressant effect (n=6).

Group 3: I/R hearts were subjected to 20 min of ischemia and perfused with 5 mL of plasma (1 mL/min) during the first 5 min of reperfusion, but were not perfused with PMNs. These hearts represented a control group to determine if 20 min of ischemia followed by reperfusion stunned the heart, but LVDP and +dP/$dt_{max}$ will recover to baseline values (initial) by the end of the 45-minute reperfusion period (n=6).

Group 4: I/R+PKC βII peptide inhibitor (10 μM, dissolved in plasma) hearts were subjected to 20 min of ischemia and not perfused with PMNs. These hearts were perfused with 5 mL of plasma+PKC βII peptide inhibitor during the first 5 min of reperfusion. This group was employed to determine if the PKC βII peptide inhibitor causes a cardiodepressant effect in the setting of I/R without PMNs (n=6).

Group 5: I/R+PMNs hearts were subjected to 20 min of ischemia and perfused with 5 mL of plasma (1 mL/min) and PMNs (resuspended in 5 mL Krebs buffer) during the first 5 min of reperfusion. These hearts represented a control group to determine if 20 min of ischemia followed by 45 min reperfusion in the presence of PMNs ($200 \times 10^6$) resulted in a sustained cardiac contractile dysfunction throughout the 45 min reperfusion period compared to initial baseline values (n=9).

Group 6: I/R+PMNs+PKC βII peptide inhibitor (1 μM) hearts were subjected to 20 min of ischemia and perfused with 1 μM PKC βII peptide inhibitor (dissolved in plasma) and PMNs ($200 \times 10^6$) during the first 5 minutes of reperfusion. These hearts represented a group to determine the effect of PKC βII inhibition in attenuating PMN-induced cardiac contractile dysfunction (n=6).

Group 7: I/R+PMNs+PKC βII peptide inhibitor (5 μM) hearts were subjected to 20 min of ischemia and perfused with 5 μM PKC βII peptide inhibitor (dissolved in plasma) and PMNs ($200 \times 10^6$) during the first 5 minutes of reperfusion. These hearts represented a group to determine the effect of PKC βII inhibition at a higher concentration of the PKC βII peptide inhibitor in attenuating PMN-induced cardiac contractile dysfunction (n=7).

Group 8: I/R+PMNs+PKC βII peptide inhibitor (10 μM) hearts were subjected to 20 min of ischemia and perfused with 10 μM PKC βII peptide inhibitor (dissolved in plasma) and PMNs ($200 \times 10^6$) during the first 5 minutes of reperfusion. These hearts represented a group to determine the effect of PKC βII inhibition at a higher concentration of the PKC βII peptide inhibitor in attenuating PMN-induced cardiac contractile dysfunction (n=7).

Group 9: I/R+PMNs+PKC βII peptide inhibitor (10 μM)+ $N^G$-nitro-L-arginine methyl ester (L-NAME, 50 μM) hearts were subjected to 20 min of ischemia and perfused with 10 μM PKC βII peptide inhibitor (dissolved in 5 mL plasma) and 50 μM L-NAME (dissolved in Krebs buffer from 50 mM stock in $H_2O$) and PMNs ($200 \times 10^6$) during the first 5 minutes of reperfusion. The L-NAME (50 μM) was continually infused into the heart throughout the 45 min reperfusion period. These hearts represented a group to determine if the cardioprotective effect of PKC βII peptide inhibition can be blocked with a nitric oxide synthase inhibitor (L-NAME) (n=6).

Previous studies showed that sham I/R hearts given PMNs exhibited no changes from initial control values (Lefer et al., *Circulation* 100: 178-184, 1999). Data were recorded every 5 min for 45 min post-reperfusion. After each experiment, the left ventricle was isolated, fixed in 4% paraformaldehyde and stored at 4° C. for later histological analysis.

Figure 7:
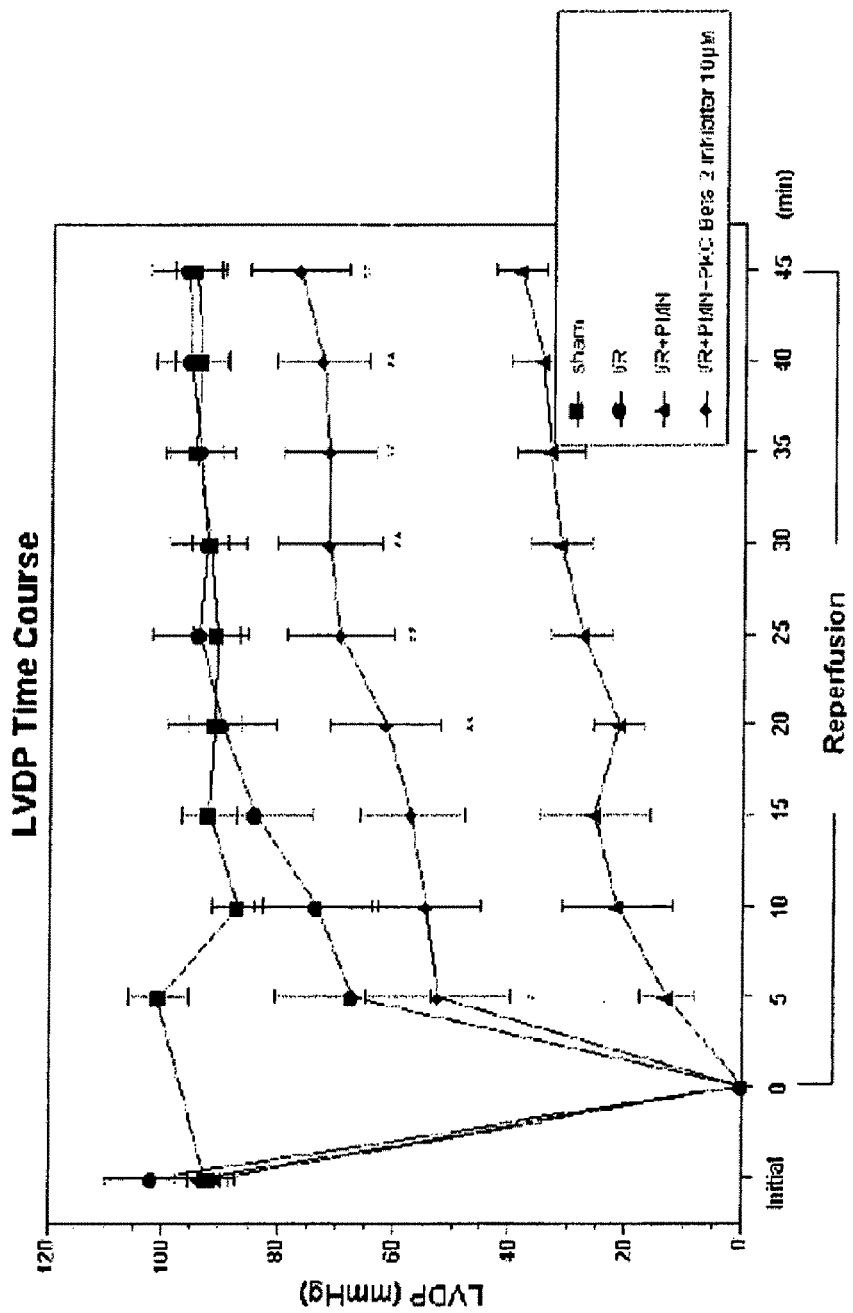
FIG. 7. Time course of LVDP in Sham I/R, I/R, I/R+PMNs and I/R+PMN+βII peptide inhibitor (10 μM) perfused rat hearts. LVDP data at initial (baseline) and reperfusion from 0 to 45 min following 20 min ischemia. The sham group (n=6) maintained the same LVDP throughout the 80 min. protocol. The I/R+PMN group (n=9) exhibited a significant and sustained reduction in LVDP compared to I/R (n=6) and I/R+PMN+βII peptide inhibitor (n=7) groups. All values are expressed as mean±SEM. *$p<0.05$ and **$p<0.01$, from I/R+PMNs.

FIG. 7 showed the time course of cardiac contractile function (LVDP) for the sham I/R, I/R, I/R+PMN+PKC βII peptide inhibitor (10 μM) and I/R+PMN groups, and illustrated the changes in LVDP during the 80 min perfusion period. The hearts in the Sham I/R group remained at 103±4% of initial baseline values of LVDP for the entire duration of the perfusion period. Hearts in the I/R group experienced a depression in LVDP during the initial stages of reperfusion, but by the end of reperfusion they had recovered to 94±6% of initial baseline values. However, the hearts in the I/R+PMN group exhibited severe cardiac contractile dysfunction, only recovering to 43±5% of initial baseline values by the end of reperfusion. By contrast, the hearts in the I/R+PMN+PKC βII peptide inhibitor (10 μM), although initially showing a depression in LVDP of 61±10% of initial baseline values at 15 min into reperfusion, recovered to 82±9% of baseline.

In order to establish whether the PKC βII peptide inhibitor produced any direct inotropic effects on cardiac contractile function, Sham I/R hearts were perfused with PKC βII peptide inhibitor (10 μM). This group served as one of the controls for the study. These hearts did not show any significant change in LVDP (FIG. 8) or +dP/$dt_{max}$ (FIG. 9) at the end of the 80 min reperfusion period, thus, indicating that at this dose the PKC βII peptide inhibitor had no direct effect on cardiac contractile function. A 20 μM dose of PKC βII peptide inhibitor was tested on a Sham I/R heart and there were no cardiodepressant effects noticed at this dose.

Figure 8:
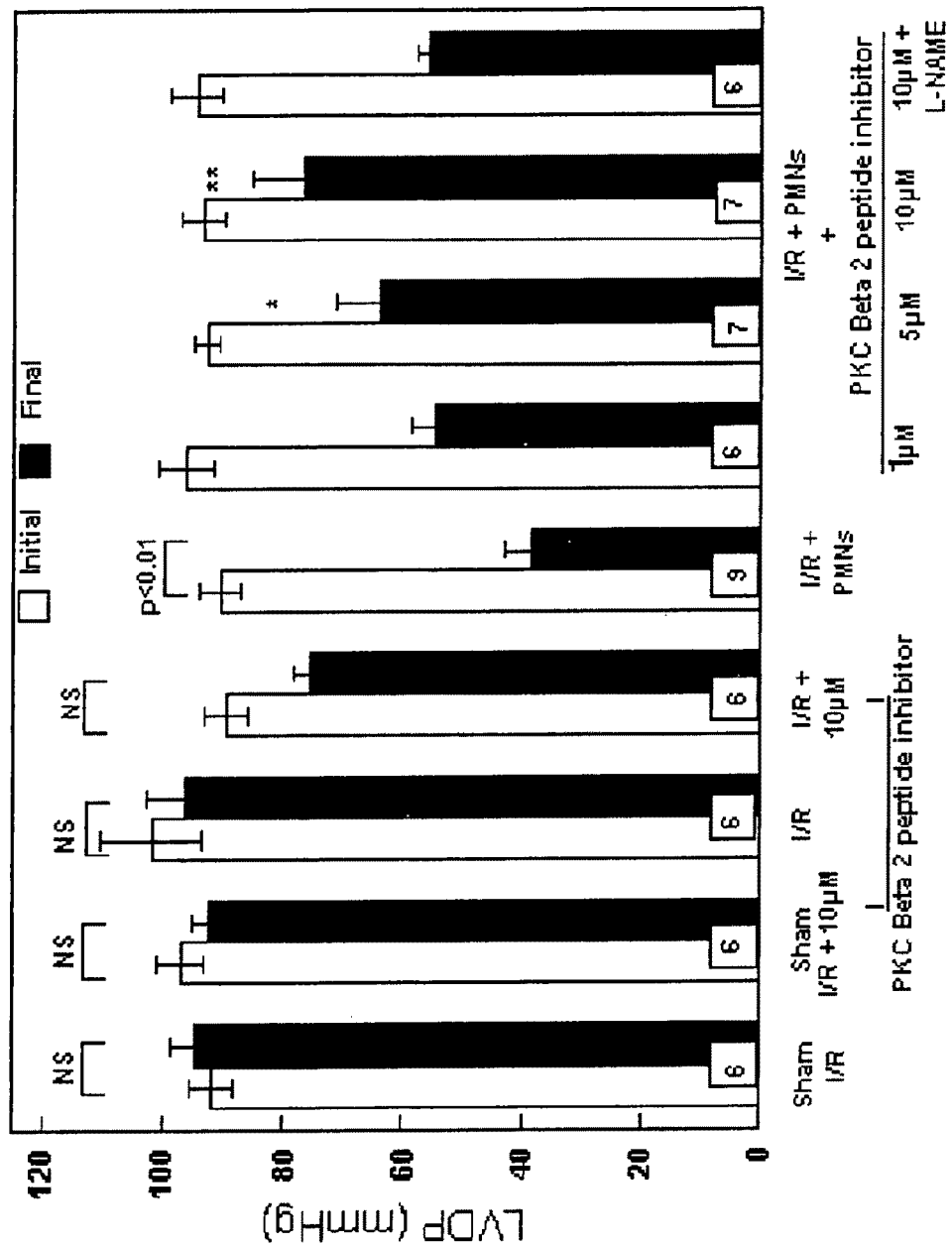
FIG. 8. Initial and final LVDP expressed in mmHg from isolated perfused rat hearts before ischemia (I) (initial) and after 45 min post reperfusion (R) (final). Hearts were perfused in the presence or absence or PMNs. PMNs induced a significant contractile dysfunction, which was attenuated by PKC βII peptide inhibitor, but was significantly blocked by the presence of L-NAME. All values are expressed as mean±SEM. Numbers of hearts examined are at the bottom of the bars. *$p<0.05$ and **$p<0.01$, from final I/R+PMNs; NS=not significant.
Figure 9:
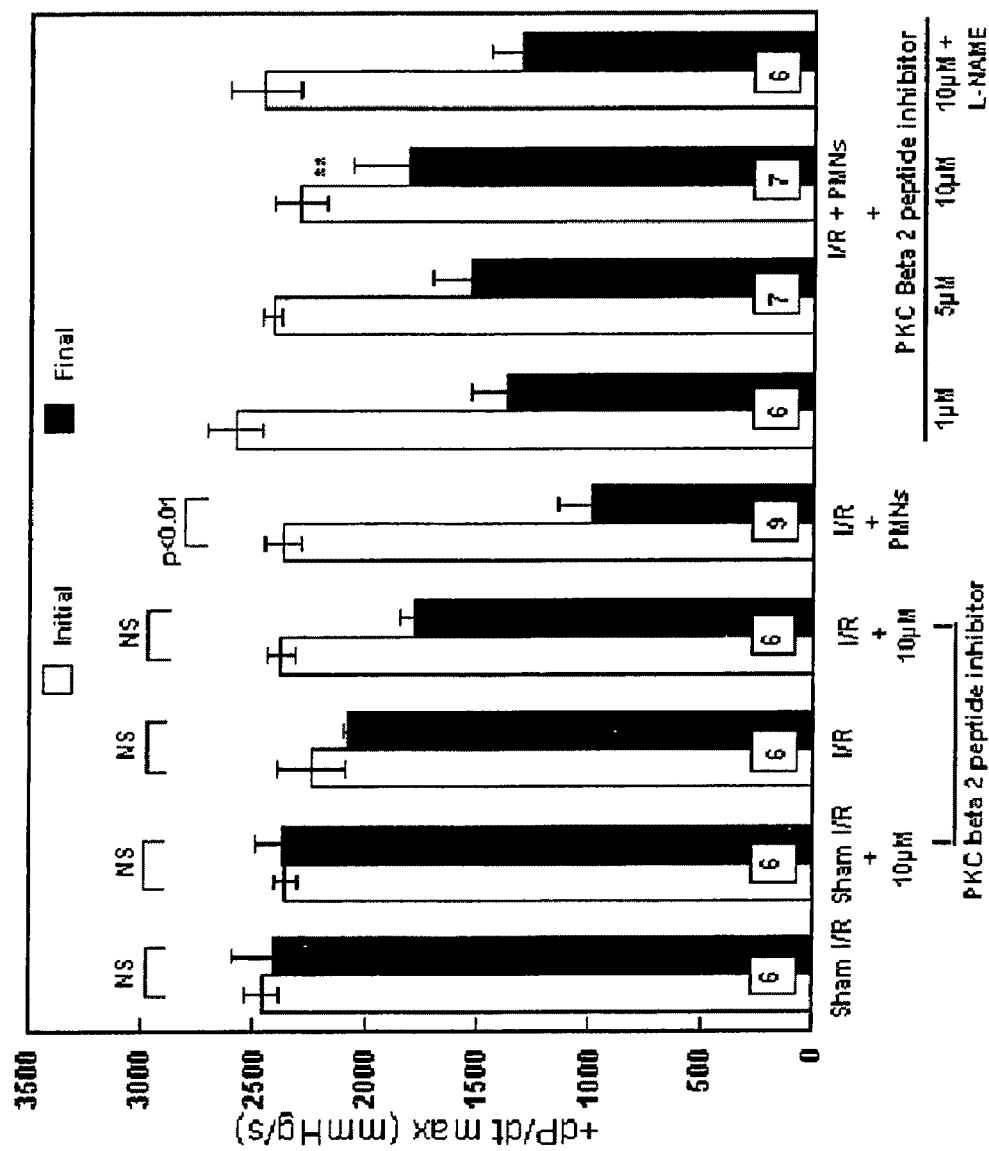
FIG. 9. Initial and final +dP/dt max expressed in mmHg/s in isolated perfused rat hearts before ischemia (I) and after reperfusion (R). Hearts were perfused in the presence or absence of PMNs. PMNs induced a significant contractile dysfunction, which was attenuated by PKC βII peptide inhibitor, but was blocked by L-NAME. All values are expressed as means±SEM. Numbers of hearts examined are at the bottom of the bars. *$p<0.05$ and **$P<0.01$, from final I/R+PMNs; NS=not significant.

FIGS. 8 and 9 showed the initial and final values for LVDP and +dP/$dt_{max}$ from isolated perfused hearts respectively. There was no significant difference between the initial baseline values of all the groups studied. There was also no significant difference between the initial and final values of LVDP and +dP/$dt_{max}$ for the Sham I/R, I/R, Sham I/R+PKC βII peptide inhibitor (5 μM), and I/R+PKC βII peptide inhibitor (10 μM) groups. However, there was a significant difference between the initial and final values of LVDP and +dP/$dt_{max}$ for the I/R+PMN group. A significant decrease (p<0.01) from initial baseline of 43±5% in LVDP and 42±6% in +dP/$dt_{max}$ at 45 min post-reperfusion was observed.

The presence of the PKC βII peptide inhibitor at a 5 μM and 10 μM dose attenuated the decrease in LVDP and +dP/$dt_{max}$ associated with the post-ischemic perfusion with PMNs. The 10 μM dose the was the most cardioprotective as the hearts in the I/R+PMN+PKC βII peptide inhibitor (10 μM) recovered to 82±9% and 79±10% of initial baseline at 45 min post-reperfusion for LVDP and +dP/dt$_{max}$, respectively. These values were significantly different from I/R+PMN at 45 min post-reperfusion (p<0.01). The 5 μM dose was also cardioprotective, although not to the same extent as the 10 μM dose, as the hearts in the I/R+PMN+PKC βII peptide inhibitor (5 μM) recovered to 69±7% and 63±7% for LVDP and +dP/dt$_{max}$ of initial baseline at 45 min post-reperfusion, respectively. The LVDP values for the 5 μM dose were significantly different from I/R+PMN at 45 min post-reperfusion (p<0.05). The 1 μM dose of PKC βII peptide inhibitor was not cardioprotective as the hearts in the I/R+PMN+PKC βII peptide inhibitor (1 μM) group only recovered to 57±4% and 53±6% for LVDP and +dP/dt$_{max}$ respectively. The final values of LVDP and +dP/dt$_{max}$ at the 1 μM dose group were not significantly different from the final values of the I/R+PMN group.

The cardioprotective effects of the PKC βII peptide inhibitor (10 μM) were blocked by the presence of L-NAME (50 μM) in the IR+PMN+PKC βII peptide inhibitor (10 μM)+ L-NAME (50 μM) group, as the LVDP and +dP/dt$_{max}$ values at the end of the 45 min reperfusion period were only 56±2% and 53±5% of the initial baseline values, respectively, and were not significantly different from the final values of the IR+PMN group (FIGS. 3 and 4).

Figure 10:
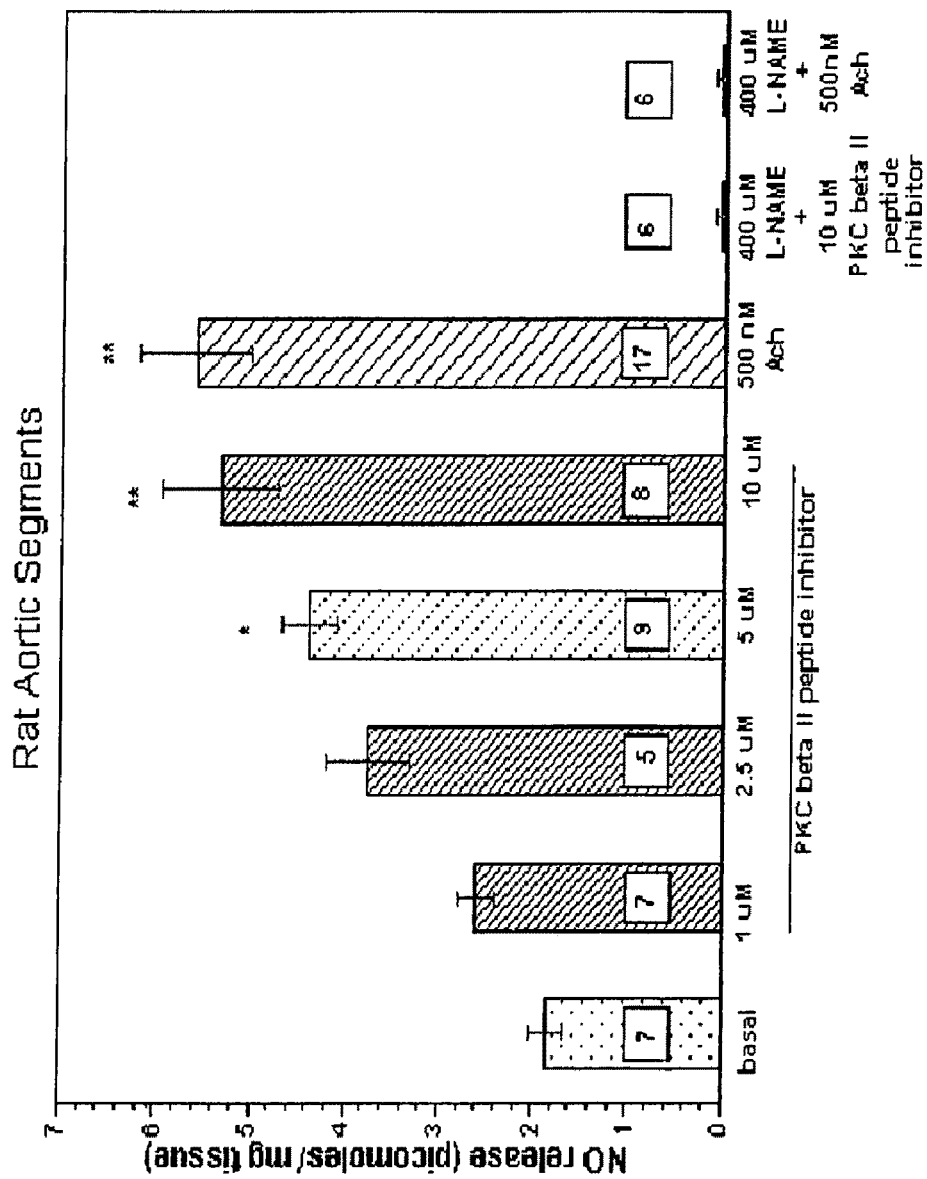
FIG. 10. Measurement of NO release from rat aortic segments. Endothelial NO release was significantly increased from basal NO release in PKC βII peptide inhibitor treated segments (1, 2.5, 5 and 10 μM), as well as acetylcholine (Ach, 500 nM). NO release was significantly reduced in both groups given 400 μM L-NAME. All values are expressed as means±SEM. Numbers at bottom of bars are numbers of separate experiments per group. *$p<0.05$, **$p<0.01$, from basal values.

NO release from rat aortic endothelium was measured to determine if PKC βII peptide inhibitor provides cardioprotection by a mechanism involving increased endothelial NO release. FIG. 10 showed that segments of the endothelium treated with PKC βII peptide inhibitor generated significantly more NO when compared to the basal NO release at 5 μM (p<0.05) and 10 μM (p<0.01). The basal value of NO release was measured at 1.85±0.18 pmoles NO/mg tissue. There was a definite dose-response effect of stimulating the endothelium with PKC βII peptide inhibitor as the 1 μM, 2.5 μM, 5 μM and 10 μM produced an increase in NO release above basal of 0.75±0.19, 1.91±0.44, 2.54±0.29, and 3.49±0.62 pmoles NO/mg tissue, respectively.

Acetylcholine (Ach, 500 nM) was used as a positive control in this assay and stimulated the endothelium causing an increase of 3.75±0.58 pmoles NO/mg tissue, above the baseline basal value. L-NAME was used as another control in order to decrease basal release of NO to zero. Both the acetylcholine and PKC βII peptide inhibitor production of NO were completely inhibited by treating the endothelium with L-NAME (400 μM).

Figure 11:
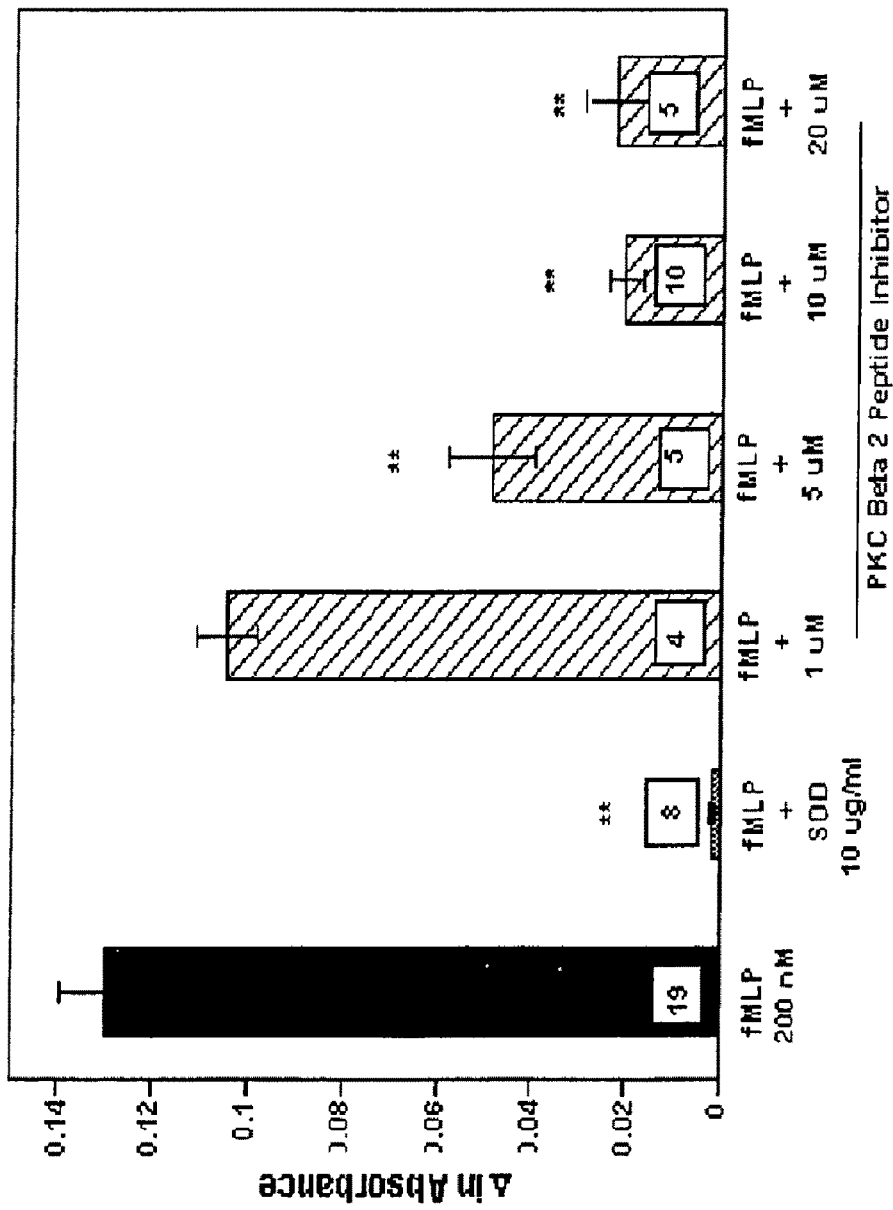
FIG. 11. Superoxide release from rat PMNs. Superoxide release was measured from $5\times10^6$ PMNs after formyl-methionyl-leucyl-phenylalanine (fMLP) (200 nM) stimulation. SOD (10 μg/ml) was employed as a positive control. The change in absorbance (Δ) was measured 90 sec after fMLP addition (peak response). Superoxide release was significantly inhibited by the PKC βII peptide inhibitor (**$p<0.01$, 5, 10 and 20 μM). All values are means±SEM. Numbers at bottom of bars are numbers of separate experiments per group.

Another mechanism that may contribute to the cardioprotective effects (i.e. LVDP) of the PKC βII peptide inhibitor may be inhibition of PMN superoxide release. PKC βII peptide inhibitor significantly inhibited superoxide release (i.e. absorbance) from suspensions of fMLP-stimulated rat PMNS from 0.13±30.01 to 0.05±0.009 (p<0.01), 0.02±0.004 (p<0.01), and 0.02±007 (p<0.01) for 5 μM, 10 μM and 20 μM respectively (FIG. 11). There was no significant inhibition of superoxide at the 1 μM dose. SOD (10 μg/ml) was used as a positive control and it scavenged the superoxide released by the fMLP-stimulated rat PMNs reducing the response to 0.0016±0.0006.

Example 3

Effects of Peptide Inhibitors of PKC βII and PKC ζ in Combination

Experiments with PKC βII and PKC C peptide inhibitors were performed substantially as described in Examples 1 and 2.

The following groups of isolated perfused rat hearts were used:

Group 1: Sham I/R hearts were not subjected to ischemia and were not perfused with PMNs, but were perfused with 5 mL of plasma (1 mL/min) at 35 minutes into perfusion (the same time point that I/R hearts would be given 5 mL of plasma, 15 minutes of baseline recordings plus 20 minutes ischemia). These hearts represented a control group to determine if the isolated rat heart can maintain LVDP and +dP/dt$_{max}$ throughout the 80-minute protocol (n=6).

Group 2: Sham I/R+PKC βII (10 μM)+PKC ζ (5 μM) peptide inhibitors hearts were not subjected to ischemia and not perfused with PMNs. These hearts were administered the PKC βII and PKC C peptide inhibitor (10 μM and 5 μM, respectively, dissolved in plasma from a 5 mM stock in H$_2$O) 35 minutes into perfusion. This group was employed to determine if the peptide inhibitors cause a cardiotonic or cardiodepressant effect (n=6).

Group 3: I/R hearts were subjected to 20 min of ischemia and perfused with 5 mL of plasma (1 mL/min) during the first 5 min of reperfusion, but were not perfused with PMNs. These hearts represented a control group to determine if 20 min of ischemia followed by reperfusion stunned the heart, but LVDP and +dP/dt$_{max}$ will recover to baseline values (initial) by the end of the 45-minute reperfusion period (n=6).

Group 4: I/R+PKC βII (10 μM)+PKC ζ (5 μM) peptide inhibitors (dissolved in plasma) hearts were subjected to 20 min of ischemia and not perfused with PMNs. These hearts were perfused with 5 mL of plasma+PKC βII+PKC ζ peptide inhibitors during the first 5 min of reperfusion. This group was employed to determine if the peptide inhibitors cause a cardiodepressant effect in the setting of I/R without PMNs (n=6).

Group 5: I/R+PMNs hearts were subjected to 20 min of ischemia and perfused with 5 mL of plasma (1 mL/min) and PMNs (resuspended in 5 mL Krebs buffer) during the first 5 min of reperfusion. These hearts represented a control group to determine if 20 min of ischemia followed by 45 min reperfusion in the presence of PMNs (200×10$^6$) resulted in a sustained cardiac contractile dysfunction throughout the 45 min reperfusion period compared to initial baseline values (n=11).

Group 6: I/R+PMNs+PKC βII (5 μM)+PKC ζ (2.5 μM) peptide inhibitors hearts were subjected to 20 min of ischemia and perfused with 1 μM PKC βII peptide inhibitor (dissolved in plasma) and PMNs (200×10$^6$) during the first 5 minutes of reperfusion. These hearts represented a group to determine the effect of PKC βII inhibition in attenuating PMN-induced cardiac contractile dysfunction (n=7).

Group 7: I/R+PMNs+PKC βII (10 μM)+PKC ζ (2.5 μM) peptide inhibitors hearts were subjected to 20 min of ischemia and perfused with 5 μM PKC βII peptide inhibitor (dissolved in plasma) and PMNs (200×10$^6$) during the first 5 minutes of reperfusion. These hearts represented a group to determine the effect of PKC βII inhibition at a higher concentration of the PKC βII peptide inhibitor in attenuating PMN-induced cardiac contractile dysfunction (n=6).

Group 8: I/R+PMNs+PKC βII (10 μM)+PKC ζ (5 μM) peptide inhibitors hearts were subjected to 20 min of ischemia and perfused with 10 μM PKC βII peptide inhibitor (dissolved in plasma) and PMNs (200×10$^6$) during the first 5 minutes of reperfusion. These hearts represented a group to determine the effect of PKC βII inhibition at a higher concentration of the PKC βII peptide inhibitor in attenuating PMN-induced cardiac contractile dysfunction (n=7).

Group 9: I/R+PMNs+PKC βII (10 βM)+PKC ζ (5 μM) peptide inhibitors+N-nitro-L-arginine methyl ester (L-NAME, 50 μM) hearts were subjected to 20 min of ischemia and perfused with 10 μM PKC βII and 5 μM PKC ζ peptide inhibitor (dissolved in 5 mL plasma) and 50 μM L-NAME (dissolved in Krebs buffer from 50 mM stock in $H_2O$) and PMNs ($200\times10^6$) during the first 5 minutes of reperfusion. The L-NAME (50 μM) was continually infused into the heart throughout the 45 min reperfusion period. These hearts represented a group to determine if the cardioprotective effect of the peptide inhibitors can be blocked with a nitric oxide synthase inhibitor (L-NAME) (n=5).

Figure 12:
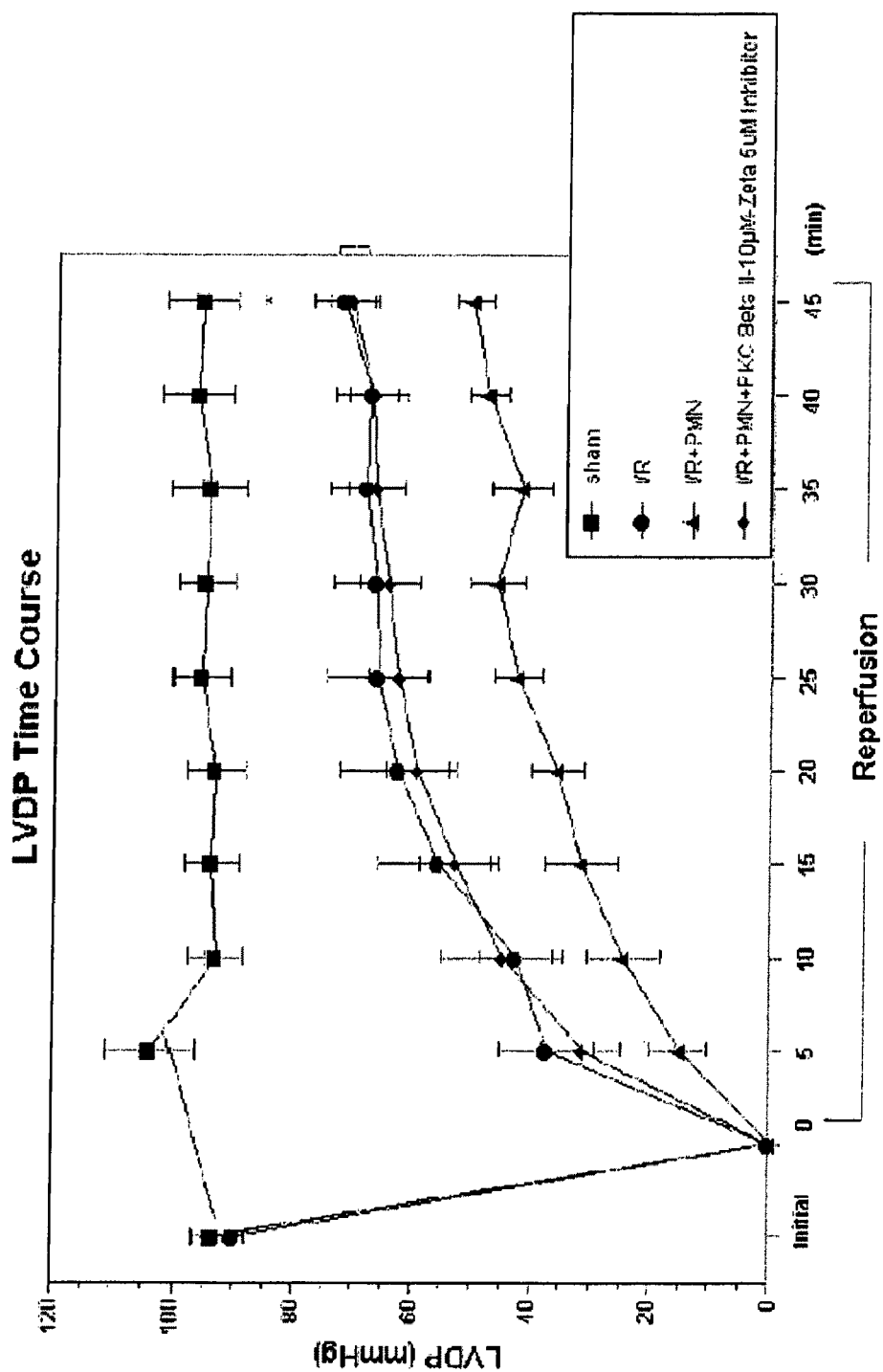
FIG. 12. Time course of LVDP in sham, I/R, I/R+PMNs and I/R+PMN+PKC βII (10 μM)+PKCζ (5 μM) peptide inhibitors perfused rat hearts. LVDP data at initial (baseline) and reperfusion from 0 to 45 min following 20 min ischemia. The sham group (n=6) maintained the same LVDP throughout the 80 min. protocol. The I/R (n=6) group partially recovered toward initial baseline values. I/R+PMN group (n=11) exhibited a significant and sustained reduction in LVDP compared to and I/R+PMN+PKC βII (10 μM)+PKCζ (5 μM) peptide inhibitors (n=7) group. All values are expressed as mean±SEM. *$p<0.05$ from I/R+PMNs.

From the time course of FIG. 12, the combination of PKC βII (10 μM) and PKC ζ (5 μM) peptide inhibitors resulted in a recovery rate matching that of the I/R heart. This result was not observed when either PKC βII (10 μM) or PKC ζ (5 μM) peptide inhibitor was used alone (Examples 1 and 2) where the recovery rate of the peptide inhibitor treated heart was slower than that of the I/R heart.

Figure 13:
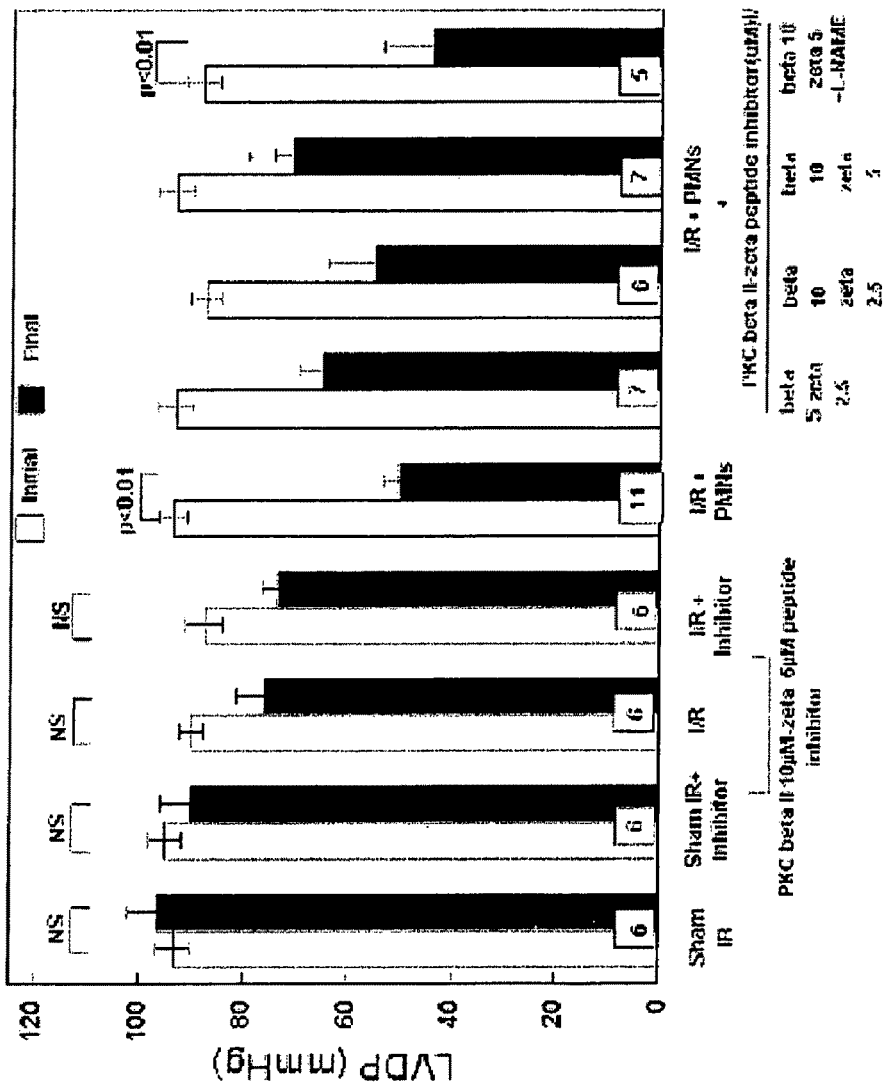
FIG. 13. Initial and final LVDP expressed in mmHg from isolated perfused rat hearts before ischemia (I) (initial) and after 45 min post reperfusion (R) (final). Hearts were perfused in the presence or absence or PMNs. PMNs induced a significant contractile dysfunction, which was attenuated by the presence of PKC βII and PKCζ peptide inhibitors. This protective effect was blocked by L-NAME. All values are expressed as mean±SEM. Numbers of hearts examined are at the bottom of the bars. *p<0.05 from final I/R+PMNs; NS=not significant.
Figure 14:
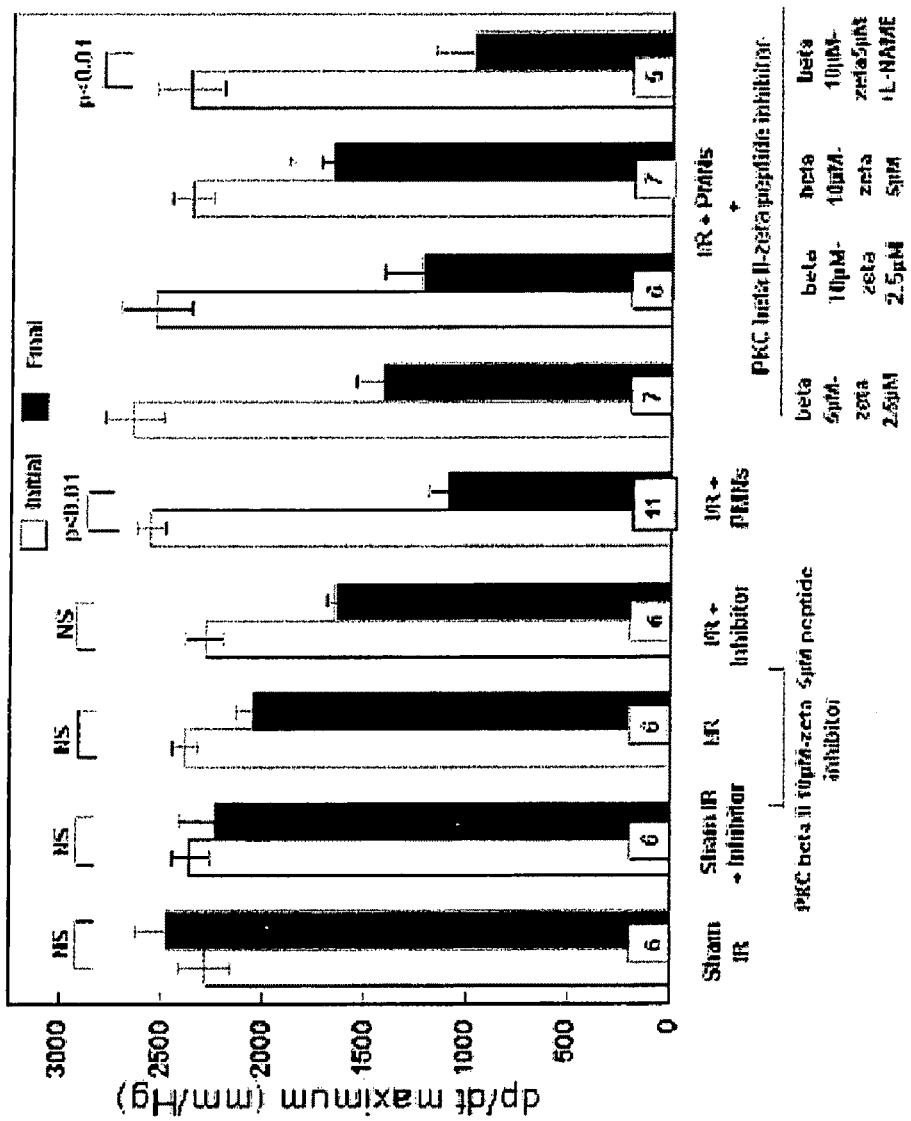
FIG. 14. Initial and final +dP/dt max expressed in mmHg/s in isolated perfused rat hearts before ischemia (I) and after reperfusion (R). Hearts were perfused in the presence or absence of PMNs. PMNs induced a significant contractile dysfunction, which was attenuated by PKC βII and PKCζ peptide inhibitors. This protective effect was blocked by L-NAME. All values are expressed as means±SEM. Numbers of hearts examined are at the bottom of the bars. *P<0.05 from final I/R+PMNs; NS=not significant.

FIGS. 13 and 14 showed the initial and final values for LVDP and +dP/$dt_{max}$ from isolated perfused hearts respectively. As expected and similar to Examples 1 and 2, the initial and final values of LVDP and +dP/$dt_{max}$ for the I/R+PMN group change significantly, decreasing (p<0.01) from initial baseline by about 50% in LVDP and by about 45% in +dP/$dt_{max}$ at 45 min post-reperfusion.

The presence of the PKC βII and PKC ζ peptide inhibitors attenuated the decrease in LVDP and +dP/$dt_{max}$ associated with the post-ischemic perfusion with PMNs. The 10 μM PKC βII and 5 μM PKC ζ peptide inhibitors dose was the most cardioprotective. Increasing the PKC βII peptide inhibitors dosage from 5 μM to 10 μM did not result in a significant change in the cardioprotective effect. On the other hand, increasing the PKC ζ peptide inhibitors dosage from 2.5 μM to 5 μM resulted in a marginal increase in the cardioprotective effect.

The cardioprotective effects of the combination of PKC βII and PKC ζ peptide inhibitors were blocked by the presence of L-NAME (50 μM) in the I/R+PMNs+PKC βII (10 μM)+PKC ζ (5 μM) peptide inhibitors+L-NAME (50 μM) group, as the LVDP and +dP/$dt_{max}$ values at the end of the 45 min reperfusion period were only about 50% and 40% of the initial baseline values, respectively, and were not significantly different from the final values of the IR+PMN group (FIGS. 13 and 14).

Figure 15:
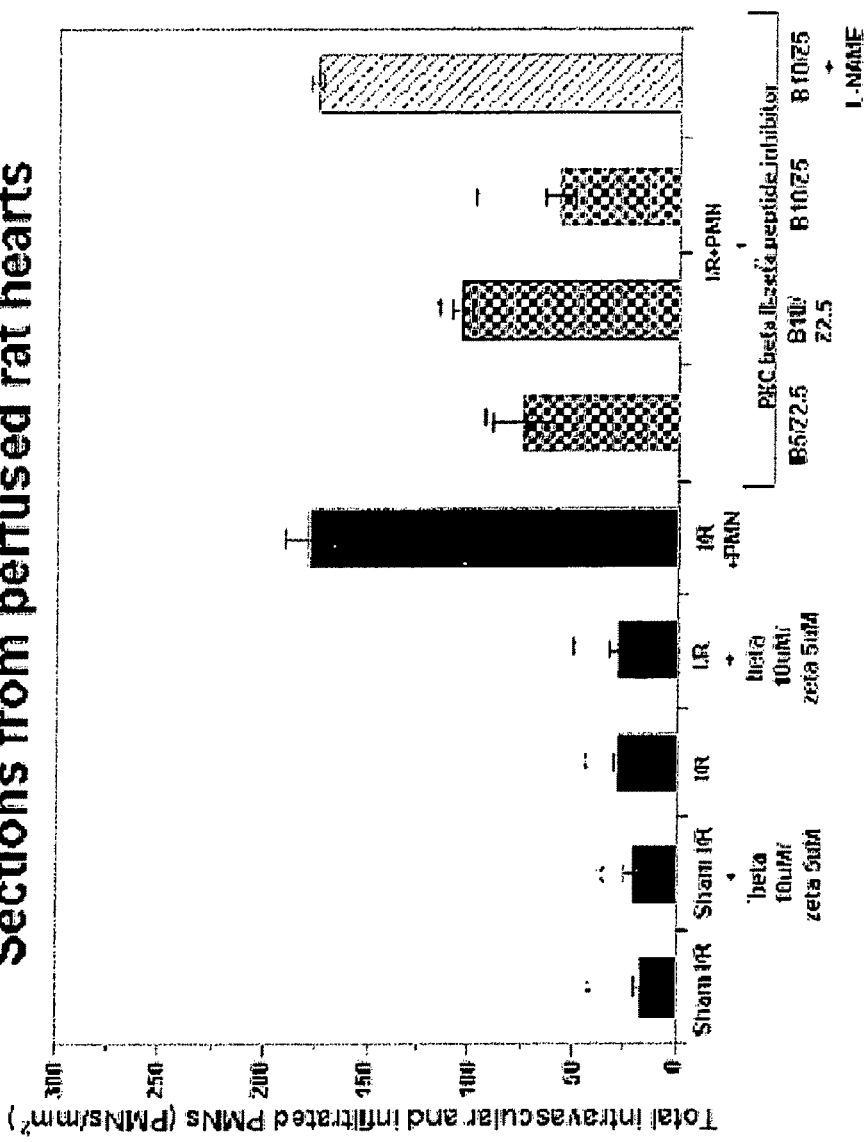
FIG. 15. Histological assessment of total intravascular and infiltrated PMNs in isolated perfused rat heart samples taken from 3 rats per group and 10 areas per heart. The numbers of total intravascular and infiltrated PMNs in post-reperfusion cardiac tissue and adhering to coronary vasculature was significantly attenuated by the PKC βII and PKC ζ peptide inhibitors. Hatched boxes represent non-PMN perfused hearts and black boxes represent PMN-perfused hearts. **P<0.01, from I/R+PMNs.

The cardiac injury associated with I/R in this model was closely correlated with the substantial number of PMNs infiltrating the myocardium within the 45 min reperfusion period. During reperfusion, a significant number of PMNs transmigrated into the myocardium, increasing from less than 25 PMN/mm$^2$ in Sham I/R hearts to more than 175 PMN/mm$^2$ in I/R+PMN hearts at the end of the reperfusion period (FIG. 15). In contrast, I/R+PMN+PKC βII+PKC ζ peptide inhibitors treated hearts experienced a significant reduction in PMN infiltration into the post-reperfused cardiac tissue. This effect was blocked in the presence of L-NAME. Furthermore, doubling the PKC βII peptide inhibitor dosage from 5 μM to 10 μM, while maintaining the PKC ζ peptide inhibitor dosage at 2.5 μM, did not significantly decrease the PMN infiltration. On the other hand, doubling the PKC ζ peptide inhibitor dosage from 2.5 μM to 5 μM, while maintaining the PKC βII peptide inhibitor dosage at 10 μM, marginally decrease the PMN infiltration (FIG. 15).

Figure 16:
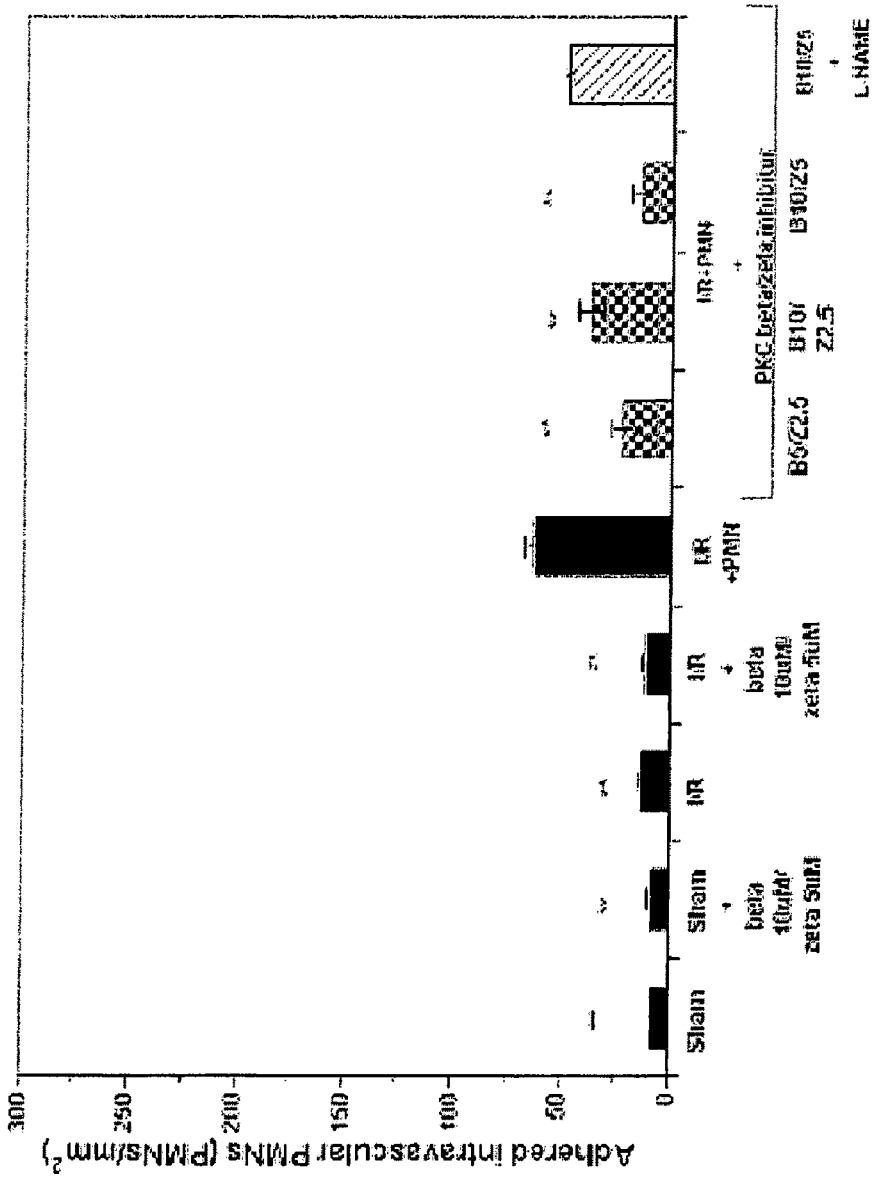
FIG. 16. Histological assessment of intravascular PMNs that adhered to the coronary vasculature in isolated perfused rat heart. The numbers of PMNs adhering to the coronary vasculature in hearts treated with PKC βII and PKC ζ peptide inhibitors was lower than I/R+PMN hearts. Hatched boxes represent non-PMN perfused hearts and black boxes represent PMN-perfused hearts. All values are mean numbers of PMNs/mm$^2$ of heart area±SEM. **P<0.01, from I/R+PMNs.

PMN adherence to coronary vascular endothelium was also evaluated within the assessment of total intravascular and infiltrated PMNs. As seen in FIG. 16, the number of adherent PMNs to the coronary endothelium was reduced in I/R+PMN+PKC βII+PKC ζ peptide inhibitors hearts. This protective effect was reversed in the presence of L-NAME.

Figure 17:
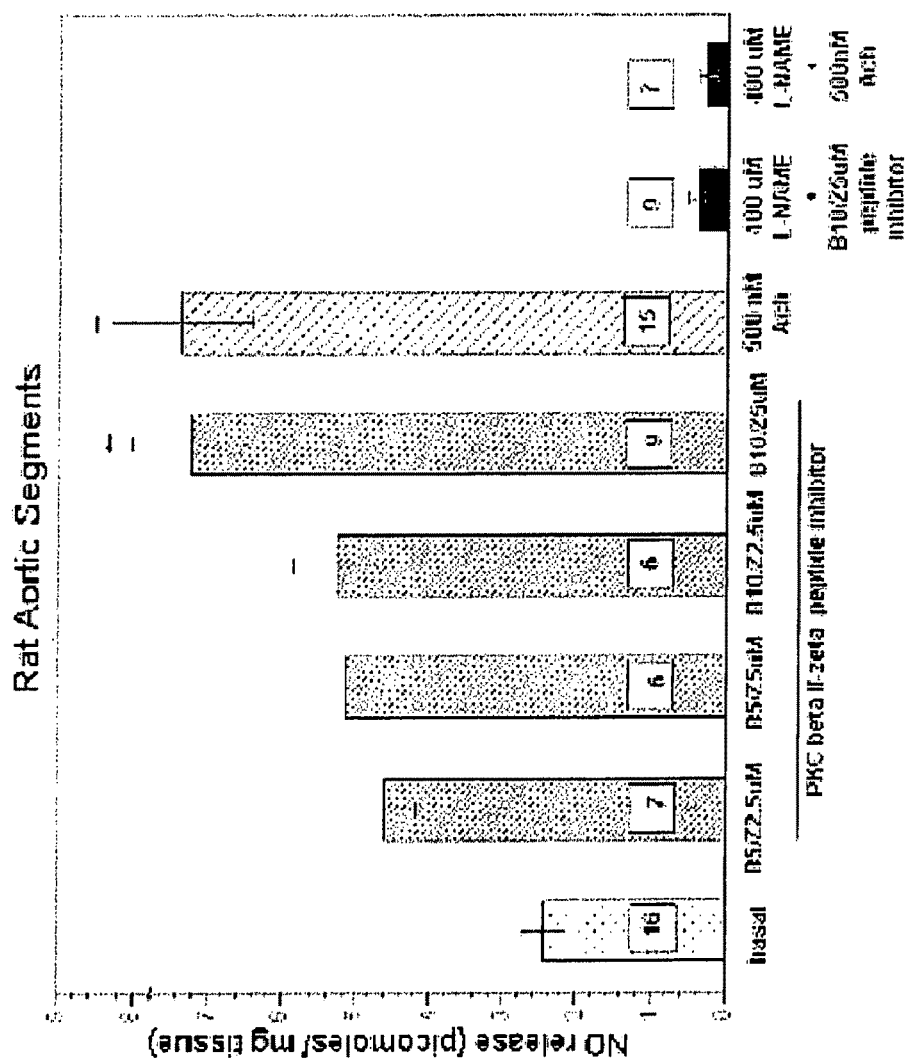
FIG. 17. Measurement of NO release from rat aortic segments. Endothelial NO release was significantly increased from basal NO release in treated segments treated with PKC βII and PKC ζ peptide inhibitors, as well as acetylcholine (Ach, 500 nM). NO release was significantly reduced in both groups given 400 μM L-NAME. All values are expressed as means±SEM. Numbers at bottom of bars are numbers of separate experiments per group. **p<0.01, from basal values.

In FIG. 17, endothelium of hearts treated with PKC βII and PKC ζ peptide inhibitors generated significantly more NO release, particularly at a dosage of 10 μM PKC βII and 5 μM PKC ζ peptide inhibitors, compared to basal NO release. Acetylcholine (500 nM) was used as a positive control in the NO assay, and significantly increased NO release compared to basal NO release. L-NAME was used as another control in order to decrease basal release of NO to zero. Both the acetylcholine and the peptide inhibitors-induced production of NO were completely inhibited by treating the endothelium with L-NAME (400 μM).

Figure 18:
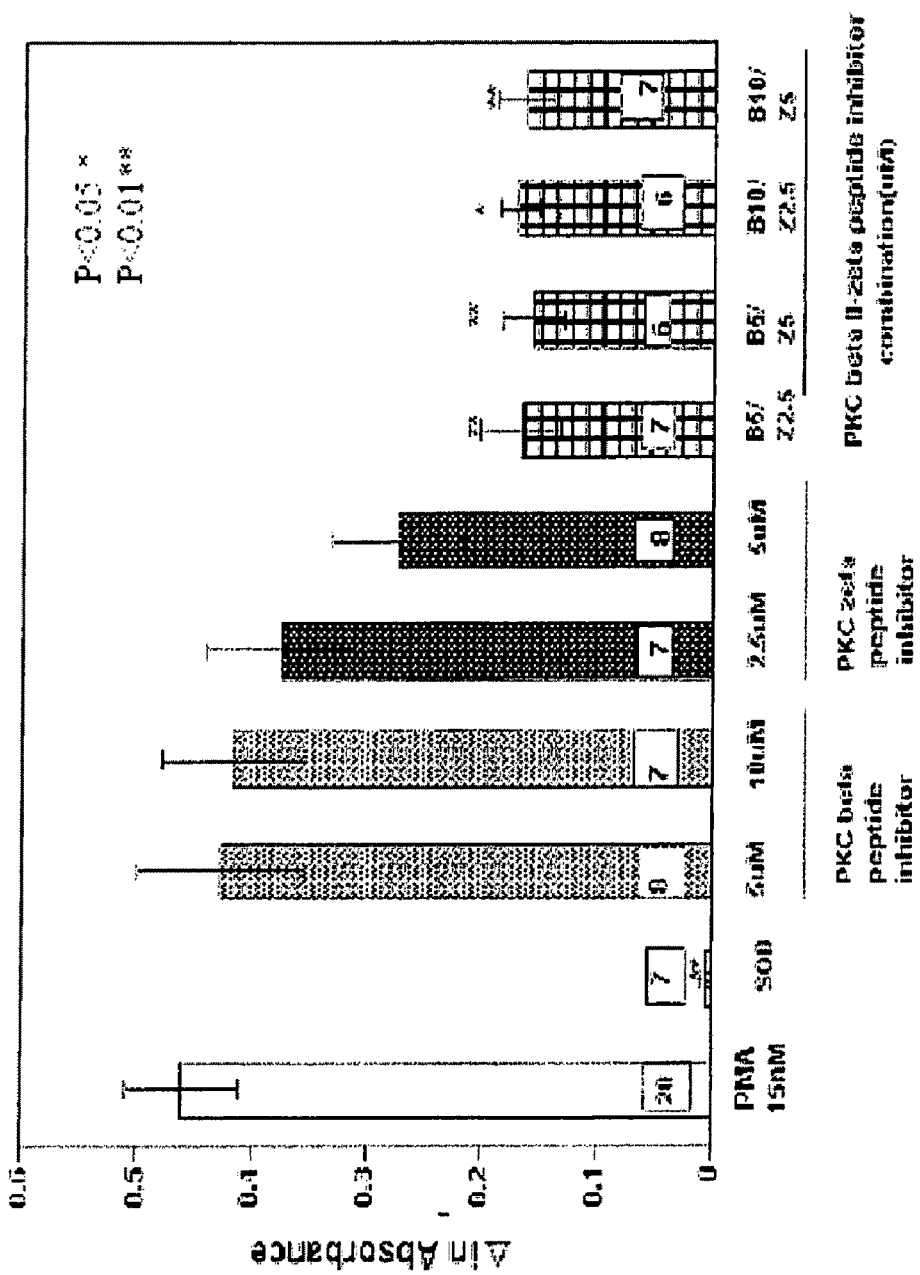
FIG. 18. Superoxide release from rat PMNs. Superoxide release was measured from 5×10$^6$ PMNs after PMA (15 nM) stimulation. SOD (10 μg/ml) was employed as a positive control. The change in absorbance (Δ) was measured 360 sec after PMA addition (peak response). Superoxide release was significantly inhibited by the presence of PKC βII and PKC ζ peptide inhibitors (*p<0.05, **p<0.01). All values are means±SEM. Numbers at bottom of bars show the numbers of separate experiments per group.

Another mechanism of the cardioprotective effects of PKC βII and PKC ζ peptide inhibitors may be related to inhibition of superoxide release. As seen from FIG. 18, the combination of PKC βII and PKC G peptide inhibitors significantly inhibited superoxide release when compared to suspensions of PMA-stimulated rat PMNs or when compared to PKC βII or PKC ζ peptide inhibitor used alone. SOD (10 μg/mL) was used as a positive control in the superoxide assays, and degraded superoxide release produced by the PMA-stimulated rat PMNs by 99% (FIG. 18).

The Examples all showed that the presence of sufficient amount of PKC βII peptide inhibitor and/or PKC ζ peptide inhibitor provided significant cardioprotective effect by attenuating PMN-induced cardiac dysfunction.

Example 4

Effects of Peptide Activator of PKC δ

Experiments with PKCδ peptide activators were performed substantially as described in Example 1 for PKCζ peptide inhibitor.

The following groups of isolated perfused rat hearts were used:

Group 1: Sham I/R hearts were not subjected to ischemia and were not perfused with PMNs, but were perfused with 5 mL of plasma (1 mL/min) at 35 minutes into perfusion (the same time point that I/R hearts would be given 5 mL of plasma, 15 minutes of baseline recordings plus 20 minutes ischemia). These hearts represented a control group to determine if the isolated rat heart can maintain LVDP and +dP/$dt_{max}$ throughout the 80-minute protocol (n=6).

Group 2: Sham I/R+PKC δ peptide activator (10 μM) hearts were not subjected to ischemia and not perfused with PMNs. These hearts were administered the PKC δ peptide activator (10 μM, dissolved in plasma from a 5 mM stock in $H_2O$) 35 minutes into perfusion. This group was employed to determine if the PKC δ peptide activator causes a cardiotonic or cardiodepressant effect (n=6).

Group 3: I/R hearts were subjected to 20 min of ischemia and perfused with 5 mL of plasma (1 mL/min) during the first 5 min of reperfusion, but were not perfused with PMNs. These hearts represented a control group to determine if 20 min of ischemia followed by reperfusion stunned the heart, but LVDP and +dP/$dt_{max}$ will recover to baseline values (initial) by the end of the 45-minute reperfusion period (n=6).

Group 4: I/R+PKC δ peptide activator (10 μM, dissolved in plasma) hearts were subjected to 20 min of ischemia and not perfused with PMNs. These hearts were perfused with 5 mL of plasma+PKC δ peptide activator during the first 5 min of reperfusion. This group was employed to determine if the PKC δ peptide activator causes a cardiodepressant effect in the setting of I/R without PMNs (n=6).

Group 5: I/R+PMNs hearts were subjected to 20 min of ischemia and perfused with 5 mL of plasma (1 mL/min) and PMNs (resuspended in 5 mL Krebs buffer) during the first 5 min of reperfusion. These hearts represented a control group to determine if 20 min of ischemia followed by 45 min reperfusion in the presence of PMNs ($200\times10^6$) resulted in a sustained cardiac contractile dysfunction throughout the 45 min reperfusion period compared to initial baseline values (n=10).

Group 6: I/R+PMNs+PKC δ peptide activator (1 μM) hearts were subjected to 20 min of ischemia and perfused with 1 μM PKC βII peptide inhibitor (dissolved in plasma) and PMNs ($200\times10^6$) during the first 5 minutes of reperfusion. These hearts represented a group to determine the effect of PKC δ activation in attenuating PMN-induced cardiac contractile dysfunction (n=6).

Group 7: I/R+PMNs+PKC δ peptide activator (5 μM) hearts were subjected to 20 min of ischemia and perfused with 5 μM PKC βII peptide inhibitor (dissolved in plasma) and PMNs ($200\times10^6$) during the first 5 minutes of reperfusion. These hearts represented a group to determine the effect of PKC δ activation at a higher concentration of the PKC δ peptide activator in attenuating PMN-induced cardiac contractile dysfunction (n=6).

Group 8: I/R+PMNs+PKC δ peptide activator (10 μM) hearts were subjected to 20 min of ischemia and perfused with 10 μM PKC δ peptide activator (dissolved in plasma) and PMNs ($200\times10^6$) during the first 5 minutes of reperfusion. These hearts represented a group to determine the effect of PKC δ activation at a higher concentration of the PKC δ peptide activator in attenuating PMN-induced cardiac contractile dysfunction (n=6).

Previous studies showed that sham I/R hearts given PMNs exhibited no changes from initial control values (Lefer et al., *Circulation* 100: 178-184, 1999). Data were recorded every 5 min for 45 min post-reperfusion. After each experiment, the left ventricle was isolated, fixed in 4% paraformaldehyde and stored at 4° C. for later histological analysis.

Figure 19:
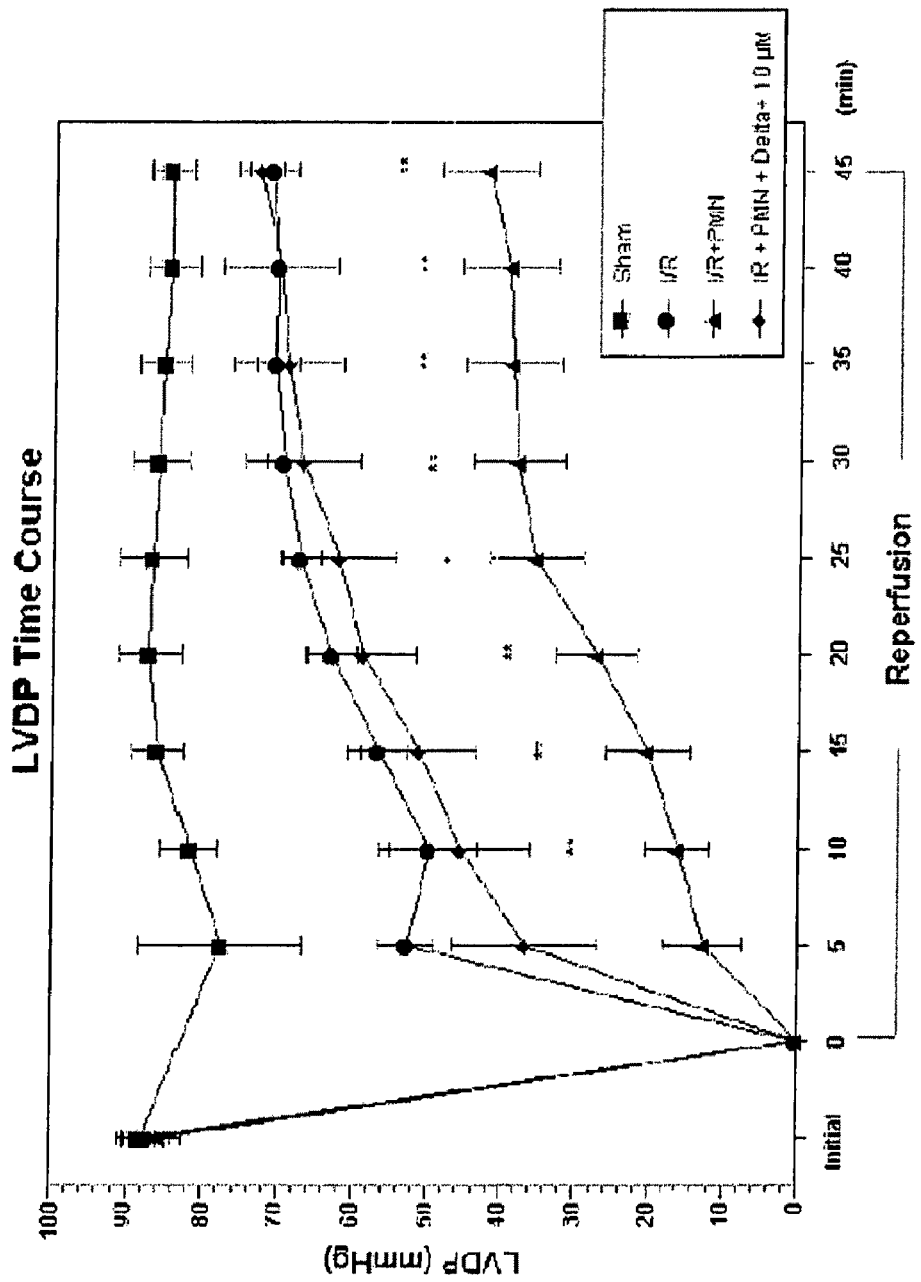
FIG. 19. Time course of LVDP in sham, I/R, I/R+PMNs and I/R+PMN+PKCδ peptide activator (10 μM) perfused rat hearts. LVDP data at initial (baseline) and reperfusion from 0 to 45 min following 20 min ischemia. The sham group (n=6) maintained the same LVDP throughout the 80 min. protocol. The I/R (n=6) group recovered to initial baseline values. I/R+PMN group (n=6) exhibited a significant and sustained reduction in LVDP compared to and I/R+PMN+PKCδ peptide activator (n=6) group. All values are expressed as mean±SEM. **p<0.01, from I/R+PMNs.

FIG. 19 showed the time course of cardiac contractile function (LVDP) for the sham I/R, I/R, I/R+PMN+PKC δ peptide activator (10 μM) and I/R+PMN groups, and illustrated the changes in LVDP during the 80 min perfusion period. The hearts in the Sham I/R group remained at 103±4% of initial baseline values of LVDP for the entire duration of the perfusion period. Hearts in the I/R group experienced a depression in LVDP during the initial stages of reperfusion, but by the end of reperfusion they had recovered to 82±3% of initial baseline values. However, the hearts in the I/R+PMN group exhibited severe cardiac contractile dysfunction, only recovering to 46±9% of initial baseline values by the end of reperfusion. By contrast, the hearts in the I/R+PMN+PKC δ peptide activator (10 μM), although initially showing a depression in LVDP of 58±8% of initial baseline values at 15 min into reperfusion, recovered to 83±3% of baseline.

In order to establish whether the PKC δ peptide activator produced any direct inotropic effects on cardiac contractile function, Sham I/R hearts were perfused with PKCε peptide inhibitor (5 μM). This group served as one of the controls for the study. These hearts did not show any significant change in LVDP (FIG. 20) or +dP/dt$_{max}$ (FIG. 21) at the end of the 45 min. reperfusion period, thus, indicating that at this dose the PKCε peptide inhibitor had no direct effect on cardiac contractile function.

Figure 20:
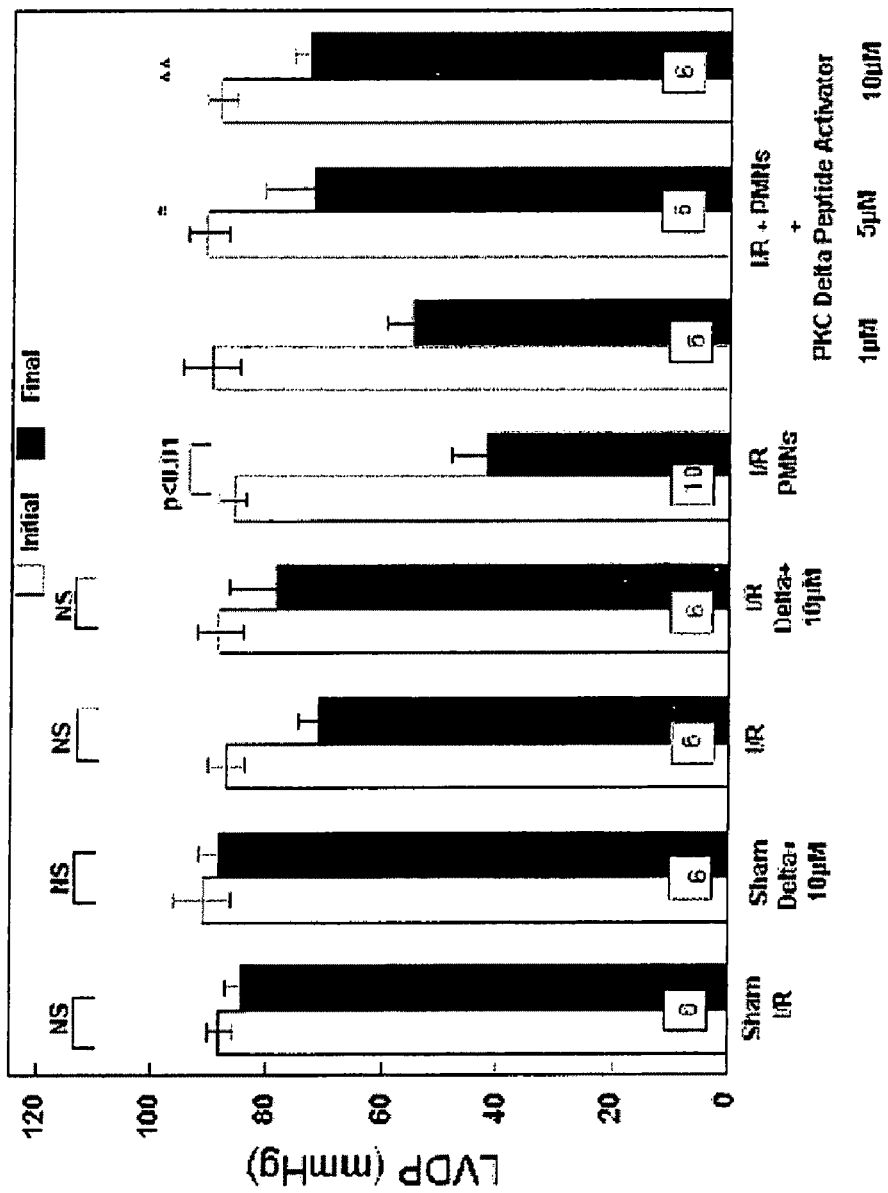
FIG. 20. Initial and final LVDP expressed in mmHg from isolated perfused rat hearts before ischemia (I) (initial) and after 45 min post reperfusion (R) (final). Hearts were perfused in the presence or absence or PMNs. PMNs induced a significant contractile dysfunction, which was attenuated by the PKCδ peptide activator. All values are expressed as mean±SEM. Numbers of hearts examined are at the bottom of the bars. *p<0.05 and **p<0.01, from final I/R+PMNs; NS=not significant.
Figure 21:
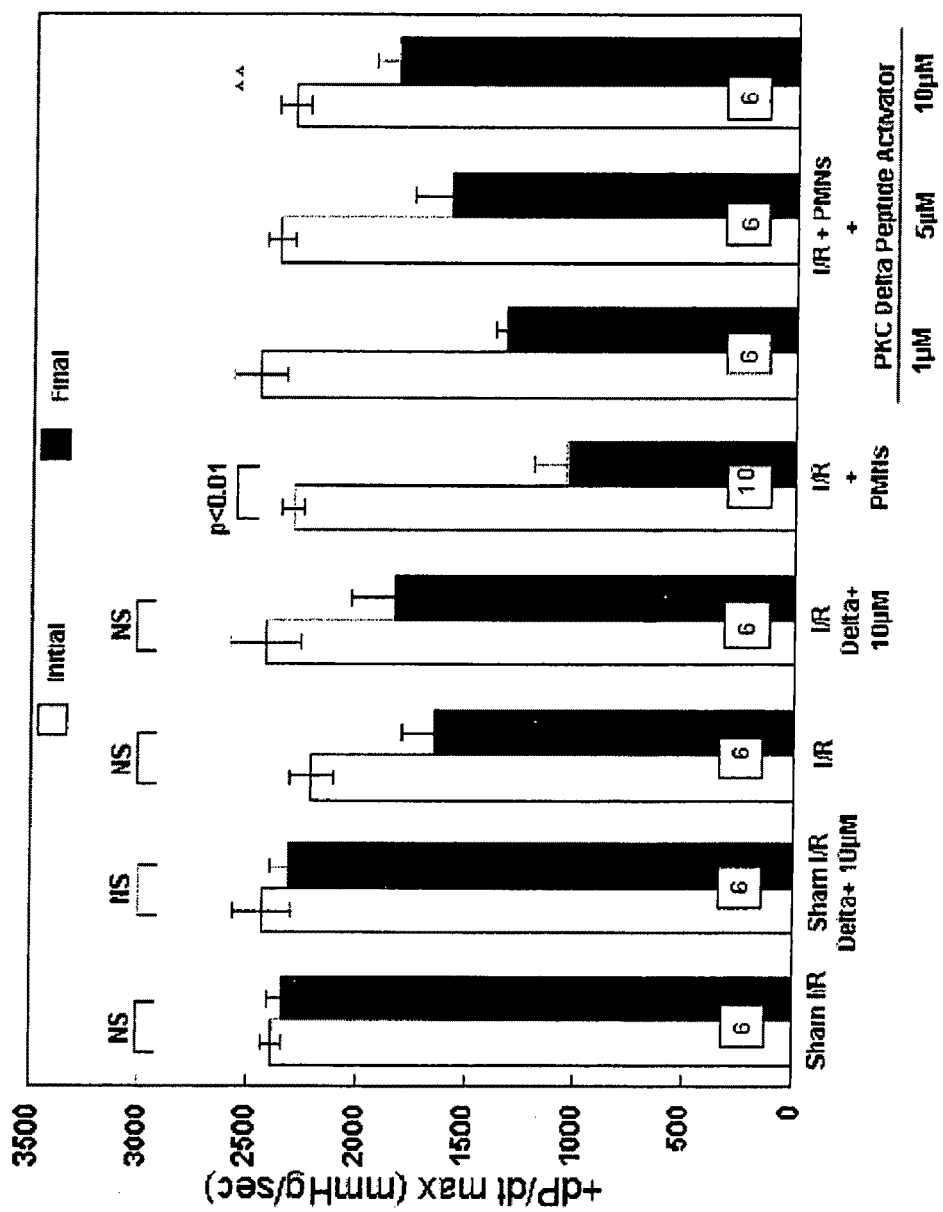
FIG. 21. Initial and final +dP/dt max expressed in mmHg/s in isolated perfused rat hearts before ischemia (I) and after reperfusion (R). Hearts were perfused in the presence or absence of PMNs. PMNs induced a significant contractile dysfunction, which was attenuated by a PKCδ peptide activator. All values are expressed as means±SEM. Numbers of hearts examined are at the bottom of the bars. **P<0.01, from final I/R+PMNs; NS=not significant.

FIGS. 20 and 21 showed the initial and final values for LVDP and +dP/dt$_{max}$ from isolated perfused hearts respectively. There was no significant difference between the initial baseline values of all the groups studied. There was also no significant difference between the initial and final values of LVDP and +dP/dt$_{max}$ for the Sham I/R, I/R, Sham I/R+PKC δ peptide activator and I/R+PKC δ peptide activator (10 μM) groups. However, there was a significant difference between the initial and final values of LVDP and +dP/dt$_{max}$ for the I/R+PMN group. A significant decrease (p<0.01) from initial baseline of 46±9% in LVDP and 45±8% in +dP/dt$_{max}$ at 45 min post-reperfusion was observed.

The presence of the PKC δ peptide activator at a 5 μM and 10 μM dose attenuated the decrease in LVDP and +dP/dt$_{max}$ associated with the post-ischemic perfusion with PMNs. The 10 μM dose the was the most cardioprotective as the hearts in the I/R+PMN+PKC δ peptide activator (10 μM) recovered to 83±3% and 79±5% of initial baseline at 45 min post-reperfusion for LVDP and +dP/dt$_{max}$, respectively. These values were significantly different from I/R+PMN at 45 min post-reperfusion (p<0.01). The 5 μM dose was also cardioprotective, although not to the same extent as the 10 μM dose, as the hearts in the I/R+PMN+PKC δ peptide activator (5 μM) recovered to 80±9% and 67±7% for LVDP and +dP/dt$_{max}$ of initial baseline at 45 min post-reperfusion, respectively. The LVDP values for the 5 μM dose were significantly different from I/R+PMN at 45 min post-reperfusion (p<0.05). The 1 μM dose of PKC δ peptide activator was not cardioprotective as the hearts in the I/R+PMN+PKC δ peptide activator (1 μM) group only recovered to 60±13% and 51±5% for LVDP and +dP/dt$_{max}$ respectively. The final values of LVDP and +dP/dt$_{max}$ at the 1 μM dose group were not significantly different from the final values of the I/R+PMN group.

Figure 22:
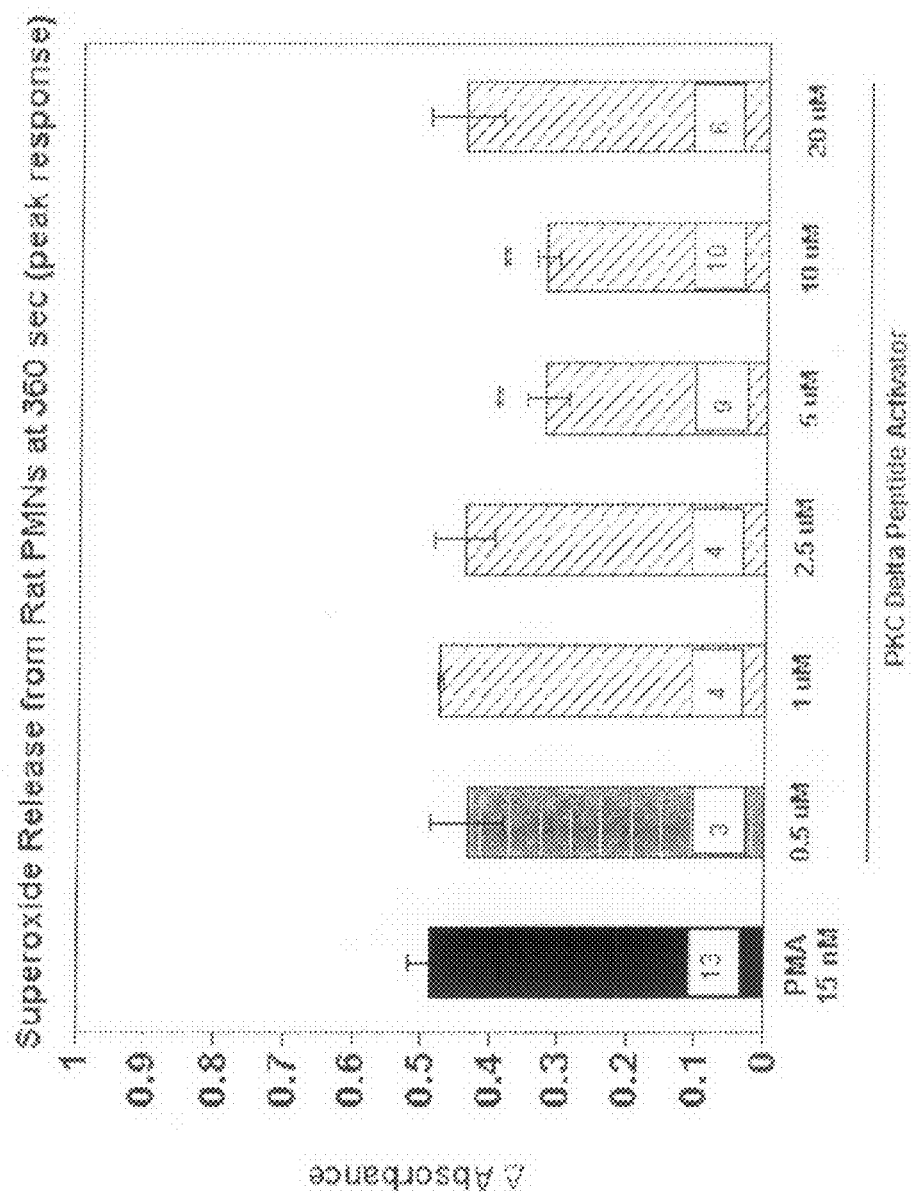
FIG. 22. Superoxide release from rat PMNs. Superoxide release was measured from 5×10$^6$ PMNs after PMA (15 nM) stimulation. The change in absorbance (Δ) was measured 360 sec after PMA addition (peak response). Superoxide release was significantly inhibited by the PKCδ peptide activator (**p<0.01, 5 and 10 μM). All values are means±SEM. Numbers at bottom of bars show the numbers of separate experiments per group.
Figure 23A:
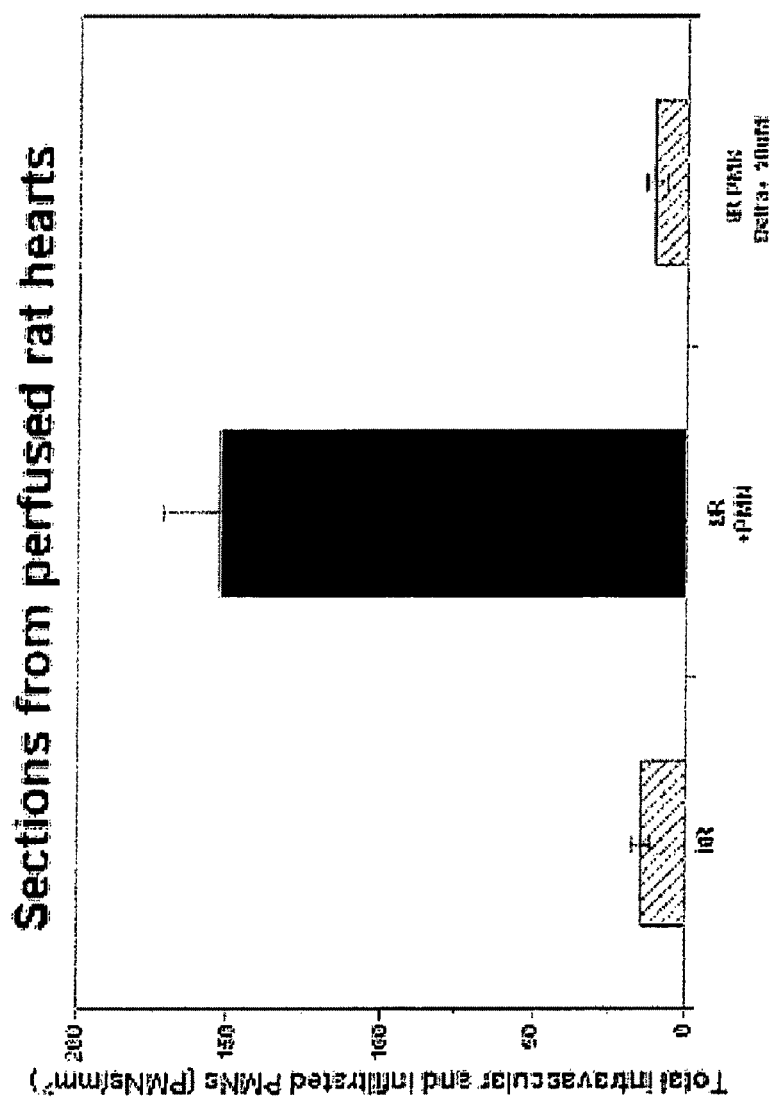
FIG. 23a. Histological assessment of total intravascular and infiltrated PMNs in isolated perfused rat heart samples taken from 3 rats per group and 10 areas per heart. The numbers of total intravascular and infiltrated PMNs in post-reperfusion cardiac tissue and adhering to coronary vasculature was attenuated by the PKCδ peptide activator. Hatched boxes represent non-PMN perfused hearts and black boxes represent PMN-perfused hearts.
Figure 23B:
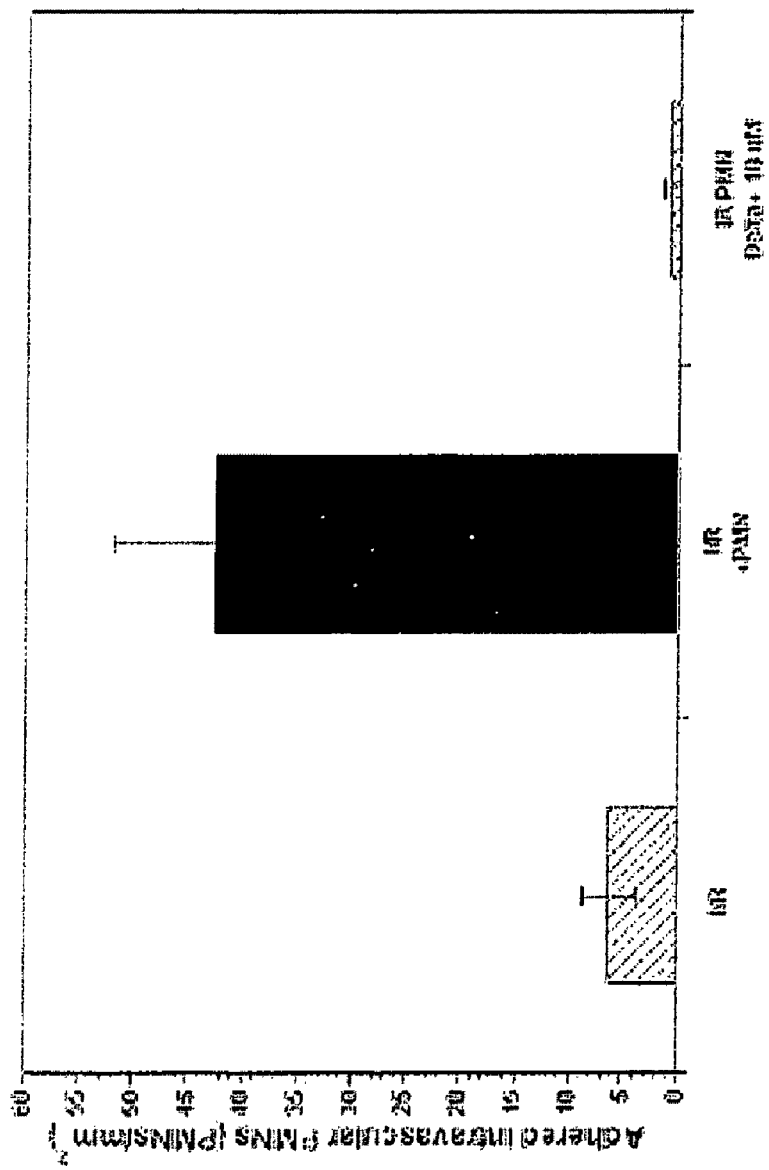
FIG. 23b. Histological assessment of intravascular PMNs that adhered to the coronary vasculature in isolated perfused rat heart samples taken from 3 rats per group and 10 areas per heart. The numbers of PMNs adhering to the coronary vasculature was attenuated by the PKCδ peptide activator. Hatched boxes represent non-PMN perfused hearts and black boxes represent PMN-perfused hearts. All values are mean numbers of PMNs/mm$^2$ of heart area±SEM.
Figure 24:
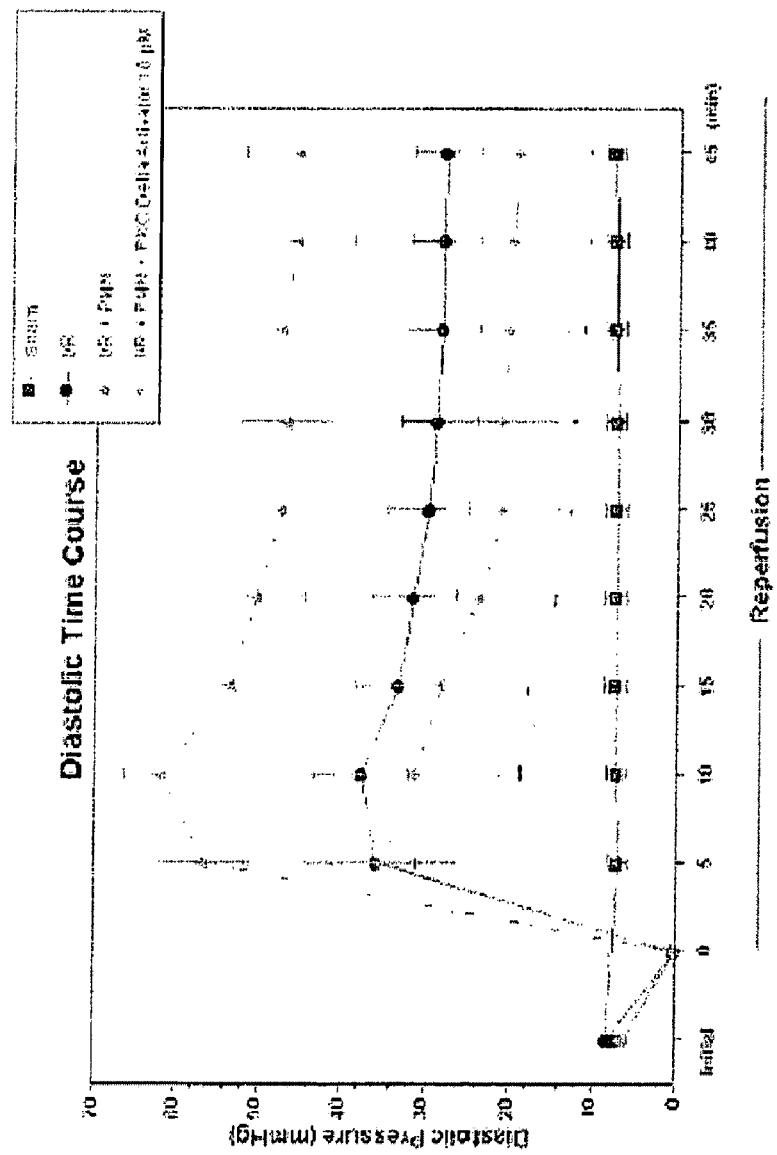
FIG. 24. Time course of left ventricular end diastolic pressure (LVEDP) in sham, I/R, I/R+PMNs and I/R+PMN+PKCδ peptide activator (10 μM) perfused rat hearts. LVEDP data at initial (baseline) and reperfusion from 0 to 45 min following 20 min ischemia. The sham group (n=6) maintained the same LVEDP throughout the 80 min. protocol. The I/R (n=6) group partially recovered to initial baseline values. I/R+PMN group (n=6) exhibited a significant and sustained elevation in LVEDP compared to and I/R+PMN+PKCδ peptide activator (n=6) group. All values are expressed as mean±SEM. *p<0.05 and **p<0.01, from I/R+PMNs.

A mechanism that may contribute to the cardioprotective effects (i.e. LVDP) of the PKC δ peptide activator may be inhibition of PMN superoxide release. PKC δ peptide activator significantly inhibited superoxide release (i.e. absorbance) from suspensions of PMA-stimulated rat PMNS from 0.49±0.03 to 0.32±0.03 (p<0.01), 0.32±0.02 (p<0.01), for 5 μM and 10 μM respectively (FIG. 22). There was no significant inhibition of superoxide at the 1 μM dose.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A method for preserving an organ for transplantation, protecting an ischemic organ from damage, attenuating organ dysfunction after ischemia, maintaining nitric oxide release in an ischemic organ, or protecting an organ from damage after isolation from the circulatory system, said method comprising the step of perfusing the organ with a solution comprising at least one peptide inhibitor of protein kinase C βII (PKCβII), wherein the inhibitor of PKCβII is a peptide of 9 amino acids in length having SEQ ID NO: 1.

2. The method of claim 1, wherein the peptide inhibitors/activator are dissolved in saline solution.

3. The method of claim 1, further comprising potassium chloride.

4. The method of claim 1, wherein the organ is a heart.

5. The method of claim 1, wherein the organ is a mammalian organ.

6. The method of claim 5, wherein the mammal is human.

7. The method of claim 1, wherein the organ is preserved for transplantation.

8. The method of claim 1, wherein the concentration of the at least one peptide inhibitor of PKCβII is about 5-10 μM.

9. The method of claim 1, wherein the at least one peptide inhibitor of PKCβII is myristoylated.

* * * * *